US008065089B1

(12) United States Patent
Najarian

(10) Patent No.: US 8,065,089 B1
(45) Date of Patent: Nov. 22, 2011

(54) METHODS AND SYSTEMS FOR ANALYSIS OF DYNAMIC BIOLOGICAL PATHWAYS

(75) Inventor: Kayvan Najarian, Concord, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 1379 days.

(21) Appl. No.: 11/603,591

(22) Filed: Nov. 22, 2006

Related U.S. Application Data

(63) Continuation-in-part of application No. 11/273,687, filed on Nov. 14, 2005, now Pat. No. 7,856,320, and a continuation-in-part of application No. 10/812,726, filed on Mar. 30, 2004, now Pat. No. 6,996,476.

(60) Provisional application No. 60/738,665, filed on Nov. 22, 2005.

(51) Int. Cl.
*G01N 33/48* (2006.01)
*C12Q 1/68* (2006.01)
*G06F 7/60* (2006.01)
*G06G 7/58* (2006.01)

(52) U.S. Cl. ............... 702/19; 435/6; 702/20; 703/2; 703/11

(58) Field of Classification Search ............... None
See application file for complete search history.

(56) References Cited

U.S. PATENT DOCUMENTS

| | | | |
|---|---|---|---|
| 6,090,555 A | 7/2000 | Fiekowsky et al. | |
| 6,144,388 A | 11/2000 | Bornstein | |
| 6,222,093 B1 | 4/2001 | Marton et al. | |
| 6,263,287 B1 | 7/2001 | Zheng et al. | |
| 6,303,301 B1 | 10/2001 | Mack | |
| 6,453,241 B1 | 9/2002 | Bassett, Jr. et al. | |
| 6,544,170 B1 * | 4/2003 | Kajihara et al. | 600/300 |
| 6,642,887 B2 | 11/2003 | Owechko | |
| 6,996,476 B2 * | 2/2006 | Najarian | 702/19 |
| 2006/0074566 A1 | 4/2006 | Najarian | |
| 2008/0294613 A1 | 11/2008 | Iyer et al. | |

OTHER PUBLICATIONS

Kauffman, "The Origins of Order: Self Organization and Selection in Evolution," Oxford University Press, New York: 1993.
Martoglio et al., "A decomposition model to track gene expression signatures: preview on observer-independent classification of ovarian cancer," Bioinformatics, 2002, 18: 1617-1624.
Notice of Allowance and Fees Due mailed Jul. 15, 2005 for U.S. Appl. No. 10/812,726.
Office Communication mailed Dec. 9, 2005 for U.S. Appl. No. 10/812,726.
*Ex Parte Quayle* Office Action mailed Feb. 9, 2005 for U.S. Appl. No. 10/812,726.
Office Action mailed Sep. 9, 2004 for U.S. Appl. No. 10/812,726.
Amendment and Response Under *Ex Parte Quayle* for U.S. Appl. No. 10/812,726 sent to USPTO on Apr. 6, 2005.
Request for Certificate of Correction of Patent for Applicant's Mistake (37 C.F.R. § 1.323) and For PTO Mistakes (37 C.F.R. § 1.322(a)) for U.S. Appl. No. 10/812,726 sent to USPTO on Oct. 3, 2006.
Communication to USPTO for U.S. Appl. No. 10/812,726 faxed to USPTO on Oct. 7, 2005.
Notice of Non-Compliant Amendment (37 CFR 1.121) mailed Jul. 25, 2007 for U.S. Appl. No. 11/273,687.
Office Action Summary mailed Sep. 7, 2006 for U.S. Appl. No. 11/273,687.
Office Action Summary mailed Jun. 15, 2006 for U.S. Appl. No. 11/273,687.
Amendment and Response Under 37 C.F.R. § 1.111 mailed to USPTO on Aug. 10, 2007 for U.S. Appl. No. 11/273,687.
Amendment and Response Under 37 C.F.R. § 1.111 mailed to USPTO on Dec. 7, 2006 for U.S. Appl. No. 11/273,687.
Election and Response mailed to USPTO on Jul. 11, 2006 for U.S. Appl. No. 11/273,687.
Preliminary Amendment mailed to USPTO on Nov. 14, 2005 for U.S. Appl. No. 11/273,687.
Office Action mailed Feb. 18, 2009 for U.S. Appl. No. 11/273,687.
United States Patent and Trademark Office, Office Action, U.S. Appl. No. 11/273,687, mailed Feb. 7, 2008.
United States Patent and Trademark Office, Office Action, U.S. Appl. No. 11/273,687, mailed Sep. 4, 2008.
Amendment and Response to Office Action under 37 CFR § 1.111, filed Jun. 6, 2008.
Amendment and Response to Final Office Action under 37 CFR § 1.116, filed Nov. 20, 2008.
United States Patent and Trademark Office, Office Action, U.S. Appl. No. 11/273,687, mailed Oct. 14, 2009.
United States Patent and Trademark Office, Office Action, U.S. Appl. No. 11/273,687, mailed May 25, 2010.
Affymetrix webpage at http://www.biospace.com/company_profile.cfm?CompanyID=1271 as available via the internet and printed on Feb. 23, 2004.
Akutsu et al., Proc. of the 1999 Pacific Symposium in Biocomputing, 4:17-28, 1999.
An IMS Mini-Meeting on Imaging, Classification, and Clustering, Department of Statistics, University of Florida, Jan. 11-12, 2002.
Arkin et al., "Stochastic Kinetic Analysis of Developmental Pathway Bifurcation in Phage λ-Infected *Escherichia coli* Cells," Genetics, 149:1633-1648, 1998.
Back, A.D. et al. "A First Application of Independent Component Analysis to Extracting Structure from Stock Returns," Int. J. Neural Syst., vol. 8, No. 5, 1-16, 473-484, 1997.

(Continued)

*Primary Examiner* — Shubo Zhou
(74) *Attorney, Agent, or Firm* — Kilpatrick Townsend & Stockton LLP

(57) ABSTRACT

Disclosed is a hierarchical computational method to predict the expression value of genes in time-series microarray data. The method may include the step of first applying a nonlinear independent component analysis (NICA) algorithm that extracts the major components covering all considered genes. An autoregressive exogenous (ARX) model may subsequently be used to quantitatively express the dynamic interactions of all components with each other. Then, using the predicted values for the components, and the nonlinear independent component analysis in the inverse form, the data may be used to predict the expression parameters for individual genes. The method may be used for the analysis of a eukaryotic gene expression throughout the cell cycle.

21 Claims, 17 Drawing Sheets

OTHER PUBLICATIONS

Bar-Joseph, Z. et al., "Comparing the Continuous Representation of Time-Series Expression Profiles to Identify Differentially Expressed Genes," Proc. Natl. Acad. Sci. USA, 100(18):10146-10151, 2003.

Bassett, D.E. Jr. et al., "Gene Expression Informatics—It's All in Your Mine," Nat. Genet. Supp., vol. 21:51-55, 1999.

Bioconductor, webpage at http://www.bioconductor.org/top.html as available via the internet and printed on Nov. 2, 2003.

Bioinformatics Graz-MPI Swarm Description http://genome.tugraz.at/Software/PathwayEditor/Description.html as available via the internet and printed on Nov. 2, 2003.

BioSieve Products—Microarray Data Analysis Software at http://www.biosieve.com/product.html as available via the internet and printed on Nov. 2, 2003.

Blohm, D.H. et al., "New Developments in Microarray Technology," Curr. Opin. Biotechnol., 12:41-47, 2001.

Bowtell, D.D.L., "Options Available—From Start to Finish—for Obtaining Expression Data by Microarray," Nat. Genet., vol. 21, Supp. 1:25-32, 1999.

Brazma, A. et al., "Gene Expression Data Analysis," FEBS Lett., 480(1):17-24, 2000.

Cheung, V.G. et al., "Making and Reading Microarrays," Nat. Genet., vol. 21, Supp. 1:15-19, 1999.

Cho, R.J., et al., "A Genome-Wide Transcriptional Analysis of the Mitotic Cell Cycle," Molecular Cell, 2:65-73, 1998.

Cluster Analysis on Microarray Data at webpage http://www.cs.bufalo.edu/~djiang3/cluster.html as available via the internet and printed on Nov. 10, 2003.

Clustering Software webpage at http://genetics.stanford.edu/~sherlock/cluster.html as available via the internet and printed on Nov. 2, 2003.

Cytoscape web page at http://www.cytoscape.org/ as available via the internet and printed on Nov. 2, 2003.

Darvish, A. et al., "A Hierarchical System Identification Technique for Modeling and Analysis of Dynamic Pathways," Bioinformatics, 2004.

Darvish, A. et al., "Discovering Dynamic Regulatory Pathway by Applying an Auto Regressive Model to Time Series DNA Microarray Data," IEEE Engineering in Medicine and Biology Society (IEEE/EMBS), Sep. 1-5, 2004.

Darvish, A. et al., "A New Hierarchical Method for Identification of Dynamic Regulatory Pathways from Time-Series DNA Microarray Data," Proceedings of the 2004 IEEE Symposium on Computational Intelligence in Bioinformatics and Computational Biology, San Diego, CA, 2004.

Darvish, A. et al., "System Identification and Independent Factor Analysis for Estimation of Dynamic Gene Regulatory Networks," Oxford University Press 2005.

Darvish, A. et al., "System Identification and Nonlinear Factor Analysis for Discovery and Visualization of Dynamic Gene Regulatory Pathways," Proceedings of the 2005 IEEE Symposium on Computational Intelligence in Bioinformatics and Computational Biology, San Diego, CA, 2005.

Devaux, F. et al., "Transcriptomes, Transcription Activators and Microarrays," FEBS Lett., 498(2-3):140-144, 2001.

Dudoit, S., "Statistical Methods and Software for the Analysis of DNA Microarray Experiments," Bioinformatics and Computational Biology Workshop, Foundation BBVA, Madrid, Apr. 25-26, 2002.

Duggan, D.J. et al., "Expression Profiling using cDNA Microarrays," Nat. Genet., Supp. 1:10-14, 1999.

Eisen et al., "Cluster Analysis and Display of Genome-Wide Expression Patterns," Proc. Natl. Acad. Sci., USA., 95:14863-14868, 1998.

Engene Gene-Expression Data Processing and Exploratory Data Analysis webpage at http://www.engene.cnb.uam.es/ as available via the internet and printed on Nov. 2, 2003.

Expression Profiler web page at http://ep.ebi.ac.uk/EP/ as available via the internet and printed on Nov. 2, 2003.

FAST-ICA: HUT—CIS web page at http://www.cis.hut.fi/projects/ica/fastica/ as available via the internet and printed on Feb. 16, 2004.

Gat-Viks et al., "Chain Functions and Scoring Functions in Genetic Networks," Bioinformatics, vol. 19, Supp. 1, i108-i117, 2003.

Gene Expression Pattern Analysis Suite (GEPAS), "Preprocessing, Viewers, Clustering, Differential Gene Expression," at http://gepas.bioinfo.cnio.es/tools.html as available via the internet and printed on Nov. 2, 2003.

Gene Network Sciences, BioMine™ 1.0, "Microarray Analysis Redefined," webpage at http://www.gnsbiotech.com/biomine.shtml as available via the internet and printed on Nov. 2, 2003.

Gene Network Sciences, BioMine™ 1.0, Experiment Design Tool,™ 2001.

GeneMaths: GenExplore—High Throughput Analysis of Gene Expression Data at http://www.applied-maths.com/ge/ge_fr2.htm as available via the internet and printed on Nov. 2, 2003.

Genesis Description at http://genome.tugraz.at/Software/Genesis/Description.html as available via the internet and printed on Nov. 2, 2003.

Genotypic Technology: Genowizard—Microarray Data Analysis System webpage at http://www.genotypictech.com/genowizard.html as available via the internet and printed on Nov. 2, 2003.

Glover, D., "DNA Cloning: A Practical Approach," vol. I, 1985.

Goodwin, B. et al., "Is Morphogenesis an Intrinsically Robust Process?" J. Theor. Biol., 163:135-144, 1993.

Greenberg, S.A., "DNA Microarray Gene Expression Analysis Technology and Its Application to Neurological Disorders," Neurology, vol. 57(5):755-761, 2001.

Hacia, J.G., "Resequencing and Mutational Analysis Using Oligonucleotide Microarrays," Nat. Genet., Supp. 1:42-47, 1999.

Harkin, D.P., "Uncovering Functionally Relevant Signaling Pathways Using Microarray-Based Expression Profiling," Oncologist, 5:501-507, 2000.

Hartemink et al., "Combining Location and Expression Data for Principled Discovery of Genetic Regulatory Network Models," Pac. Symp. Biocomput., 437-439, 2002.

Hedge, P. et al., "A Concise Guide to cDNA Microarray Analysis—II," Biotechniques, 29(3):548-562, 2000.

Holloway, A.J. et al., "Options Available—From Start to Finish—for Obtaining Data from DNA Microarrays II," Nat. Genet., 32 Supp. 1:481-489, 2002.

Hori, G. et al., "Blind Gene Classification Based on ICA or Microarray Data," ICA 2001 Meeting, San Diego, USA, p. 332-336.

Hughes, T.R. et al., "DNA Microarrays for Expression Profiling," Curr. Opin. Chem. Biol., 5:21-25, 2001.

HumanaNow, "Statistical Issues in cDNA Microarray Data Analysis," webpage at http://biomed.humanapress.com/ChapterDetail.pasp?isbn=1-59259-364-X&ccode=1-5925 as available via the internet and printed on Nov. 2, 2003.

IFMBE News: Maide Bucolo, Sep. 2002 webpage at http://ifmbe-news.iee.org/ifmbe-news/sept2002/bucolo.html as available via the internet and printed on Nov. 10, 2003.

Jolliffe, I.T., "Principal Component Analysis," New York : Springer-Verlag, 1986.

Kholodenko, B. et al., "Untangling the wires: a strategy to trace functional interactions in signaling and gene networks," Proc. Natl. Acad. Sci., USA, 99:2841-12846, 2002.

Lappalainen, H. et al., Bayesian Non-linear Component Analysis by Multi-Layer Perceptrons, In:Advances in Independent Component Analysis, Mark Girolami ed., Sprnger, 93-121, 2000.

Lee, S.I. et al., "Application of Independent Component Analysis to Microarrays," Genome Biology, 4:R76.1-R76.21, 2003.

Liebermeister, W., "Linear Modes of Gene Expression Determined by Independent Component Analysis," Bioinformatics, 18(1):51-60, 2002.

Maniatis, T. et al., "Molecular Cloning: A Laboratory Manual," 1982.

The MathWorks: MATLAB and Simulink for Technical Computing, webpage at http://www.mathworks.com/company/contact.shtml as available via the internet and printed on Feb. 16, 2004.

"Microarray Explorer Tool for Data Mining Gene Expression Patterns," webpage at http://maexplorer.sourceforge.net/ as available via the internet and printed on Nov. 2, 2003.

"My Microarray Software Comparison—Image Analysis Software," webpage at http://ihome.cuhk.edu.hk/~b400559/arraysoft_image.html as available via the internet and printed on Nov. 2, 2003.

"My Microarray Software Comparison—Data Mining Software," webpage at http://ihome.cuhk.edu.hk/~b400559/arraysoft_mining.html as available via the internet and printed on Nov. 2, 2003.

"My Microarray Software Comparison—Data Preprocessing Software," webpage at http://ihome.cuhk.edu.hk/~b400559/arraysoft_preprocess.html as available via the internet and printed on Nov. 2, 2003.

"My Microarray Software Comparison—Statistics Software and Technical Programming Languages," webpage at http://ihome.cuhk.edu.hk/~b400559/arraysoft_statistics.html as available via the internet and printed on Nov. 2, 2003.

"My Microarray Software Comparison," webpage at http://ihome.cuhk.edu.hk/~b400559/arraysoft.html as available via the internet and printed on Nov. 2, 2003.

"My Microarray Software Comparison—Data Mining Software (Turnkey/Enterprise System)," webpage at http://ihome.cuhk.edu.hk/~b400559/arraysoft_mining_turnkey.html as available via the internet and printed on Nov. 2, 2003.

"My Microarray Software Comparison—Data Mining Software (Comprehensive Software)," webpage at http://ihome.cuhk.edu.hk/~b400559/arraysoft_mining_comprehensive.html as available via the internet and printed on Nov. 2, 2003.

"My Microarray Software Comparison—Data Mining Software (Extension of Existing Data Mining Software)," webpage at http://ihome.cuhk.edu.hk/~b400559/arraysoft_mining_extension.html as available via the internet and printed on Nov. 2, 2003.

"My Microarray Software Comparison—Network/pathway Reconstruction and Analysis Software," webpage at http://ihome.cuhk.edu.hk/~b400559/arraysoft_pathway.html as available via the internet and printed on Nov. 2, 2003.

"My Microarray Software Comparison—R Packages for Microarray Analysis," webpage at http://ihome.cuhk.edu.hk/~b400559/arraysoft_rpackages.html as available via the internet and printed on Nov. 2, 2003.

Nadon, R. et al., "Statistical Issues with Microarrays: Processing and Analysis," Trends in Genet., 18(5):265-271, 2002.

Najarian, K. et al., "Independent Component Analysis and Scoring Function Based on Protein Interactions," Proceedings of IEE International Conference Intelligent Systems, Jun. 2004.

Najarian, K. et al., "A Unified Nonlinear Signal Processing and System Identification Approach to Dynamic Pathway Identification from DNA Microarray Data," Poster Presented at Proceedings of BISTI 2003 Symposium on "Digital Biology: The Emerging Paradigm," Washington, D.C., Nov. 6-7, 2003.

Pajunen, P. et al., "Nonlinear Blind Source Separation by Self-Organizing Maps," web page at http://209.85.165.104/search?q=cache:LV7xL63Uvb0J:www.cs.helsinki.fi/u/ahyvarin/pap..., as available via the Internet and printed Mar. 13, 2007.

Partek Pattern Recognition Software, "Turning Data into Discovery," web page at http://www.partek.com/html/products/products.html, as available via the Internet and printed on Nov. 2, 2003.

Quackenbush, J., "Computational Analysis of Microarray Data," Nat. Rev. Genet., 2:418-427, 2001.

Raychaudhuri, S. et al., "Basic Microarray Analysis: Grouping and Feature Reduction," Trends in Biotechnology, 19(5):189-193, 2001.

Rosetta Features, webpage at http://rosetta.lcb.uu.se/general/features.html, as available via the Internet and printed on Nov. 2, 2003.

SAS, webpage at http://www.sas.com/contact/intro.html, as available via the Internet and printed on Feb. 16, 2004.

Schulze, A. et al., "Navigating Gene Expression Using Microarrays—A Technology Review," Nature Cell Biology, 3:E190-E195, 2001.

Sherlock, G., "Analysis of Large-Scale Gene Expression Data," Briefings in Bioinform., 2(4):350-362, 2001.

Sherlock, G., "Analysis of Large-Scale Gene Expression Data," Current Opinion in Immunology, 12:201-205, 2000.

Silicon Genetics Products, "GeneSpring; The Industry Leader ," webpage at http://www.silicongenetics.com/cgi/SiG.cgi/Products/GeneSpring/index.smf, as available via the Internet and printed on Nov. 2, 2003.

Solazzi, M. et al., "Spline Neural Networks for Blind Separation of Post-Nonlinear-Linear Mixtures," IEEE Transactions on Circuits and Systems I: Regular Papers, 51(4):817-829, 2004.

Somogyi, R. et al., "The Gene Expression Matrix: Towards the Extraction of Genetic Network Architectures," Nonlinear Analysis, Theory, Methods & Applications, vol. 30, No. 3, pp. 1815-1824, 1997.

Southern, E. et al., "Molecular Interactions on Microarrays," Nat. Genet, 21 Supp. 1:5-9, 1999.

Stone, J.V. et al., "Spatiotemporal Independent Component Analysis of Event-Related fMRI Data Using Skewed Probability Density Functions," NeuroImage, 15:407-421, 1999.

Torkkola, K. et al., "Self-Organizing Maps in Mining Gene Expression Data," Information Sciences, 139:79-96, 2001.

Toronen, P. et al., "Analysis of Gene Expression Data Using Self-Organizing Maps," FEBS Lett., 451(2):142-146, 1999.

Vigario, R.N., "Extraction of Ocular Artefacts from EEG Using Independent Component Analysis," Electroenceph. Clin. Neurophysiol., 103:395-404, 1997.

Wu,T.D., Analysing Gene Expression Date from DNA Microarrays to Identify Candidate Genes, J. Pathol., 195:53-65, 2001.

Yang, H.H. et al., "Information-Theoretic Approach to Blind Separation of Sources in Non-Linear Mixture," Signal Processing, 64, 291-300, 1998.

Yeung, K.Y. et al., "Principal Component Analysis for Clustering Gene Expression Data," Bioinformatics, 17(9):763-774, 2001.

Yeung, M.K.. et al., "Reverse Engineering Gene Networks Using Singular Value Decomposition and Robust Regression," Proc. Natl. Acad. Sci., USA, 9:6163-6168, 2002.

Yuh, C.H. et al., "Genomic Cis-Regulatory Logic: Experimental and Computational Analysis of a Sea Urchin Gene," Science, 279:1896-1902, 1998.

Makeig, S. et al., Independent Component Analysis of Electroencephalographic Data, Advances in Neural Information Processing Systems 8, D. Touretsky, M. Mozer and M. Hasselmo (Eds.), MIT Press, Cambridge MA, 145-151, 1996.

* cited by examiner

Cluster 1: Early G1 Phase

SWI4
◊ actual  * estimated

CDC46
◊ actual  * estimated

Cluster 2: Early G2 Phase

SWE1
◊ actual  * estimated

GIN4
◊ actual  * estimated

Cluster 3: S Phase

NUD1
◊ actual  * estimated

CIN8
◊ actual  * estimated

Cluster 4: G2 Phase

CSE4
◊ actual  * estimated

ELM1
◊ actual  * estimated

Cluster 5: M Phase
FIG. 4I            FIG. 4J
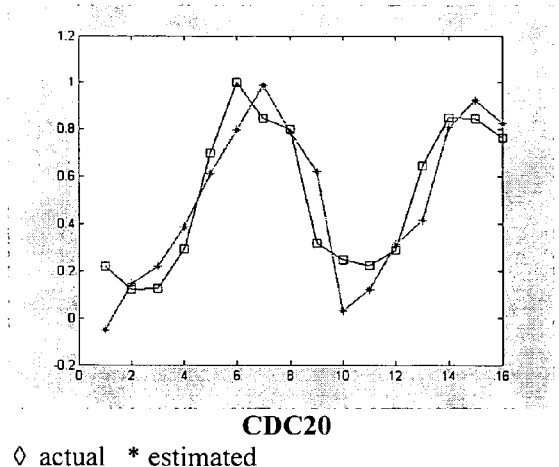
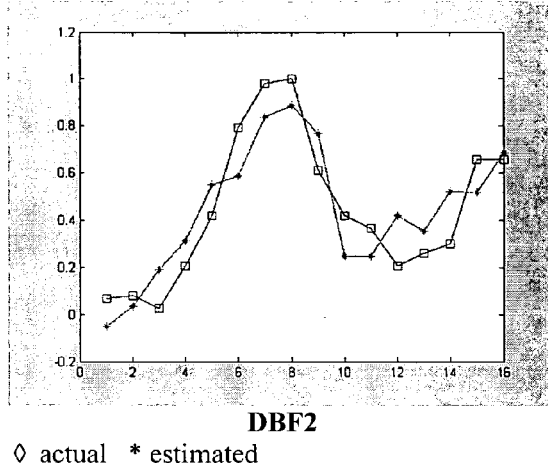
                     CDC20                                      DBF2
◊ actual   * estimated                      ◊ actual   * estimated

METHODS AND SYSTEMS FOR ANALYSIS OF DYNAMIC BIOLOGICAL PATHWAYS

RELATED APPLICATIONS

This application is a continuation-in-part of U.S. patent application Ser. No. 10/812,726, filed Mar. 30, 2004, now U.S. Pat. No. 6,996,476, and U.S. patent application Ser. No. 11/273,687, filed Nov. 14, 2005, now U.S. Pat. No. 7,856,320 and claims priority to U.S. Provisional Patent Application Ser. No. 60/738,665, filed Nov. 22, 2005. The disclosure of U.S. patent application Ser. Nos. 10/812,726, 11/273,687, and 60/738,665 are incorporated by reference in their entireties herein.

FIELD OF INVENTION

The present invention relates to methods and systems for analysis of dynamic biological pathways.

BACKGROUND

Understanding various gene regulatory networks can be of the utmost importance in addressing the molecular basis of many disease states. Characterization of gene regulatory networks may involve the estimation of the interactions among the genes involved in a given biological pathway, often using molecular biology data sets provided by high-throughout assays. The main objective of such studies is to identify regulatory networks affecting the expression level of various genes and/or the regulation of particular gene products.

Recently, DNA microarrays have become a valuable tool for exploring gene expression. DNA microarrays may be formed using fragments of genomic DNA, DNA pools generated by cloning or other amplification and/or selection techniques, or short stretches of DNA known as oligonucleotides. A single microarray chip may yield expression profiles for thousands of genes. Still, the data provided by such arrays, while fairly straightforward to generate, may provide significant challenges with respect to analysis. Often, in order for this type of research to be most productive, thousands of data points need to be directly compared in a single experiment. For example, in some cases it may be important to compare gene expression profiles over time, thus multiplying the number of data points generated from a single array by the number of time points measured.

One objective of microarray data analysis is to identify the "independent" clusters of genes, such that the genes belonging to the gene cluster have similar expression patterns that may be involved in, or required for, a specific physiological response. For example, it is expected that there may be one subset of genes required for cholesterol metabolism, a second subset involved in the immune response, and yet another subset of genes involved in the development of cancer. It would be of interest to identify these pools of genes to develop a better understanding of these processes and to identify targets for potential therapeutic agents. In most existing microarray processing technologies, the process of selecting the number of gene groups that describes the number of independent pathways is left up to the user. Incorrectly selecting the number of independent groups can skew the analysis such that vastly different results are generated depending upon how many independent gene groups are assumed.

Also, for many studies, the goal is to determine the cause-and-effect relationship by which particular genes are expressed. For example, expression of one gene may inhibit, enhance, or have no effect on the expression of a second gene. Alternatively, expression of one gene may influence another gene, but there may be a lag period. Also, the expression profile for a particular gene may be modified by changes in the environment, such as a physical change in the cell or as a result of chemical signals inducing or inhibiting expression. Extracting this type of information from array data can be a challenging task, especially when the identity and function of most of the genes under study is unknown.

A variety of approaches have been used to understand gene expression data. Many pathway identification techniques simplify the pathway identification problem by assuming only binary interactions among genes and molecules (Kauffman, S. A., "The Origins of Order, Self-Organization and Selection in Evaluation, 2003, Oxford University Press), while others attempt to quantitatively model all biochemical and/or molecular interactions (Arkin et al., Genetics, 149: 1633-1688, 1998). For example, a Random Boolean network may be used to define the state of each gene as a binary value which is affected by other genes through logical or Boolean functions (Kauffman, 1993; Gat-Viks et al., Bioinformatics, 18:i108-i117, 2003; Yuh et al., Science, 279:1896-1902, 1998). For example, such studies have been used to predict the effects of potential regulator genes on one gene (i.e. regulatee), assuming that each gene affects only one gene in a linear sequence of regulators. Also, Boolean networks may be used to handle a noisy input data (Akutsu et al., Proc. of the 1999 Pacific Symposium in Biocomputing, 17-28, 1999). While rather simple in structure and low on computational complexity, Boolean networks may not provide a realistic description of complex biological systems where small variations in the concentration of one molecule can result in dramatic changes to the system. On the other hand, the methods modeling all molecular details of the interactions among genes and molecules (often through sets of differential equations) may be limited to biological systems having a very small number of elements (genes or molecules). This is due to the fact that such models have a large number of parameters that must be reliably estimated, even for a small network of only a few genes. A more biologically-meaningful, and computationally realistic approach may apply non-binary reverse engineering to detect the regulatory network among the genes (Kholodenko et al., Proc. Natl. Acad. Sci., USA., 99:12841-12846, 2002; Yeung et al., Proc. Natl. Acad. Sci., U.S.A., 9:6163-6168, 2002; Somogyi et al., Proc. of Second World Cong. Of Nonlinear Analysts, 30:1815, 1997).

Thus, what is needed are methods and systems to analyze DNA microarray data, such as time-series data, or data that measure a particular biological cause and effect, so as to provide the information needed to characterize related groups of genes, and the dynamic regulatory pathways that may function in the cell. For example, it would be useful to predict the dynamic interaction among genes in time. Because of the complex nature of gene expression in the cell, such methods may comprise computerized systems for statistical analysis techniques. In this way, the data may be analyzed in a way that provides meaningful results.

SUMMARY

Embodiments of the present invention comprise methods and systems for analysis of dynamic biological pathways. In certain embodiments, the biological pathway is a gene expression pathway or a network that describes the expression of a plurality of genes in at least one cell type. Or, other types of biological data may be analyzed, such as data from proteomics studies, genetic mapping, data relating to posttranslational processing, data relating to nucleic acid based inhibition of gene expression, and the like.

The present invention may be embodied in a variety of ways. In an embodiment, the present invention comprises a computer-implemented method for analyzing gene expression. The method may comprise the step of compiling data comprising a plurality of measured gene expression signals into a form suitable for computer-based analysis. The method may further comprise the step of applying a nonlinear independent component analysis (NICA) or nonlinear factor analysis (NLFA) to the data to identify a plurality of independent components into which the data may be grouped. Also, the method may comprise applying dynamic mathematical modeling techniques, such as Autoregressive eXogenous (ARX) modeling or Autoregressive (AR) modeling, to the independent components defined by NICA or NLFA to describe an expression profile for at least some of the identified independent components. The method may further comprise the step of applying NICA or NLFA in the inverse manner to the expression profile model for an individual component to predict the expression values of an individual gene. In other embodiments, the present invention may comprise systems and computer-readable media for performing the methods of the invention.

For example, one embodiment of the present invention comprises a gene microarray processing technology for extracting biologically meaningful results from microarray data. Another embodiment comprises a method for the analysis of gene expression data that clusters genes having related expression profiles into optimally defined independent groups, without a need for any assumptions regarding the size and/or numbers of clusters.

Embodiments of the present invention provide certain advantages. In an embodiment, the methods and systems of the present invention provide a simplified analysis of gene expression data, while providing results that may be correlated with biologically relevant pathways. Also, the method and systems of the present invention may allow for the application of autoregressive exogenous (ARX) or autoregressive (AR) modeling to large amounts of data. The methods and systems as described herein may be adapted to the analysis of gene expression data, as well as other types of biological data. The dynamic networks and pathways revealed using the systems and methods of the present invention may be important in many bioinformatics applications including automated drug discovery.

The present invention may be better understood by reference to the following non-limiting figures, description, and claims.

DETAILED DESCRIPTION

Definitions

Figure 1:
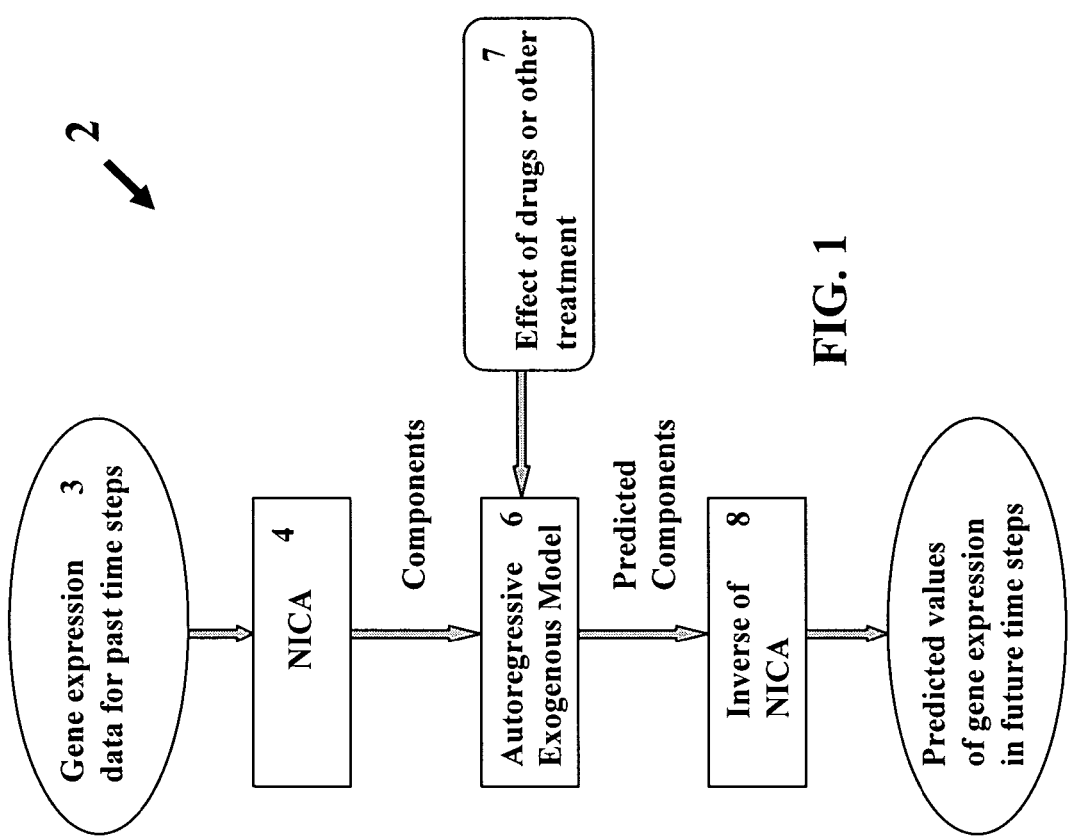
FIG. 1 shows a schematic diagram of a method for array analysis in accordance with an embodiment of the present invention in which nonlinear independent component analysis (NICA) is used in conjunction with Autoregressive eXogenous modeling (ARX) to group gene expression profiles, and an inverse analysis with NICA is used to predict the behavior of individual genes.

As used herein, the following terms shall have the definitions set out below.

In accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

DNA molecules may be identified by their nucleic acid sequences, which are generally presented in the 5' to 3' direction (as the coding strand), wherein 5' and 3' indicate the linkages formed between the 5'-hydroxy group of one nucleotide and the 3'-hydroxyl group of the next. For a coding-strand sequence presented in the 5'-3' direction, its complement (or non-coding strand) is the DNA strand which hybridizes to that sequence according to Watson-Crick base pairing.

The term "gene" means a region of DNA encoding for the mRNA sequence that codes for a given protein/polypeptide along with elements regulating mRNA expression.

"Messenger RNA" or "mRNA" shall mean an RNA molecule that encodes for a polypeptide.

"Complementary DNA" or "cDNA" shall mean the DNA molecule synthesized by polymerization of deoxyribonucleotides from an RNA template by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein, is defined as a molecule comprised of two or more deoxy- or ribonucleotides, preferably more than eight. Its exact size will depend upon many factors which, in turn, depend upon the ultimate function and use of the oligonucleotide.

A "DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species that include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

As used herein, the term "hybridization" refers generally to a technique wherein denatured RNA or DNA is combined with complementary nucleic acid sequence that is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

A polypeptide refers to any peptide generated from a protein or the full-length protein itself. A polypeptide may include the full-length protein or a fragment generated by proteolytic cleavage, chemical cleavage, or other means.

As used herein, an array or microarray is a solid-state grid containing short sequences of nucleic acid (usually DNA) of known sequence fixed at a particular position (or address) on the grid. DNA arrays are usually termed microarrays due to the small size of the grid and the small amounts of nucleotide (e.g., $\mu M$ or nM amounts) present at each address.

Dynamic biological pathways are pathways in which the interactions among the pathway elements occur over time, and/or upon the imposition of a stimulus (e.g., a chemical or a drug). For example, a dynamic gene expression pathway is a pathway in which some genes alter the expression levels of other genes after a certain time delay and according to a pattern that can change over time. In dynamic pathways, the variations in the level of a particular element, such as a chemical, protein, or a gene, can be due to the changes in the expression of other pathway elements (e.g., genes) in the previous time steps.

Independent component analysis (ICA) decomposes an input dataset into components so that each component is as statistically independent from the others as possible. ICA groups the data into groups or clusters such that the correlation for individuals within a group is maximized (i.e., intra-group samples are highly correlated), while the correlation for individuals in separate groups is minimized (i.e., samples in different groups show minimal correlation).

Iterative independent component analysis performs ICA in an iterative manner such that the analysis is performed for a successively increasing number of independent groups or clusters until the fit of the data starts to decrease. At the point where the fit of the data ceases to improve, the analysis considers the number of independent groups to be optimized.

Nonlinear independent component analysis (NICA) is the nonlinear version of a family of methods commonly referred to as independent component analysis (ICA). The purpose of linear ICA is to separate a number of source signals that are linearly combined with each other from the observations, which are the combined signals. Similarly, the objective of NICA is to separate the source signals that are nonlinearly combined with each other by processing the observed combined signals.

Nonlinear factor analysis (NLFA) is a nonlinear counterpart of principal component analysis. While a major objective of factor analysis may be dimension reduction, the method can also be used for blind separation of sources, i.e., the same problem ICA is designed for. Formulations of NLFA may be essentially equivalent to NICA. For example, the particular embodiment of NICA used herein is also a formulation used for a family of NFLA methods. As such, in many embodiments of the present invention, NLFA and NICA may be used interchangeably.

A nonlinear independent component analysis (or nonlinear factor analysis) can be used in the inverse direction, i.e., one can start from the sources and combine them using the NICA nonlinear equations to form the combined observations. FIG. 1 shows the role of this step in predicting the expressions of individual genes at the future steps. For example, use of NICA in the reverse direction is referred to herein as Inverse NICA.

As used herein, Autoregressive modeling is a technique to relate the future values of a time series to the values of the time series at the previous time steps as well as the values of other time series at the previous time steps. For example, consider the following Autoregressive eXogenous (ARX):

$$y(t)=ay(t-1)+by(t-2)+cu(t-1)+n(t)$$

where: y(t) is the output variable (such as the expression level of a group of genes), u(t) is the exogenous input (such as the dose of a certain drug), and n(t) is the noise. As can be seen, the model predicts the value of the output at time t according to the values of the output at times t−1 and t−2, and the exogenous input at time t−1. Noise is a stochastic input. If u(t) is removed from the model, i.e. no exogenous input is used, the model is reduced to an Autoregressive (AR) model, such as the following:

$$y(t)=ay(t-1)+by(t-2)+n(t)$$

where the future values of the output are predicted only based on the past values of the output.

As used herein dynamic mathematical modeling is any model in which the future/present values of a variable are related to the past values of the same variable (and possible the past values of other variables). Autoregressive (AR) modeling, Autoregressive eXogenous (ARX) modeling, and a Box-Jenkins approach are all examples of dynamic mathematical modeling.

Data fitting is a process in which a model is presented to fit all or most of the given data points.

Mutual information is an information theoretic measure that quantifies the amount of information shared by two random variables.

Information distance is an information theoretic measure that quantifies the amount of disparity and dissimilarities between the information provided by two random variables.

Hyper-volume is the multi-dimensional space occupied by a multi-dimensional variable or function.

Efficient ICA, as used herein, is a version of ICA that while maintaining the given n−1 independent components, analyzes the signals to produce the nth independent component.

Normalized data, as used here, refers to a process in which signals are standardized by removing their mean (or median) and dividing by their standard deviation (or quartile).

Variance is a measure of scattering of the data points defined based on the second order distance of the points from the mean.

As used herein, cross-correlation is understood as a dependency of expression of one element (e.g., a first gene) in the group upon the expression of a second element (e.g., a second gene) in the group. Thus, a positive cross-correlation comprises the situation in which the expression of one gene in the group is statistically correlated with the expression of a second gene in the same group such that the expression of one of the genes is dependent upon expression of the other gene.

As used herein, a computer program comprises a computer-encoded language that encodes the steps required for the computer to perform a specific task or tasks.

Also, as used herein, software comprises the computer program(s) used in conjunction with any other operating systems required for computer function.

As used herein, the singular forms "a", "an" and "the" include plural references unless the context clearly dictates otherwise.

Analysis of Dynamic Gene Expression Pathways

The present invention provides systems and methods for the analysis of data relating to dynamic biological pathways. Dynamic biological pathway may be pathways that change over time, or that change upon the imposition of a stimulus (e.g., a chemical or a drug). Using microarray analysis, an array having thousands of data points may be used to describe genes related to a specific biological or physiological process.

Certain embodiments of the present invention comprise methods and systems that efficiently address the analysis of gene array data to identify independent clusters of gene expression profiles and to describe and quantify interrelated pathways for genes within a cluster or genes that are in independent clusters. For example, the methods and systems of the present invention may be used to identify gene clusters and the interaction of particular gene groups with various environmental factors, such as the concentration of a particular drug or chemical, pH, osmolarity, or temperature. The methods and systems of the present invention may also be used to identify gene clusters and the interaction of genes within a group that are required for a particular biological response, such as the healing process, metabolism of certain compounds, the immune response, or cancer. One embodiment of the present invention comprises a computer-implemented method which may be used with a standard laboratory personal computer (PC) employing statistical software common in the art. Also described are systems using the methods of the present invention that may be used in conjunction with imaging systems and data processing systems typically used for analysis of DNA microarrays.

The present invention may be embodied in a variety of ways. In an embodiment, the present invention comprises a computer-implemented method for analyzing gene expression. The method may comprise the step of compiling data comprising a plurality of measured gene expression signals into a form suitable for computer-based analysis. The method may further comprise the step of applying a nonlinear independent component analysis (NICA) to the data to identify a plurality of independent components into which the data may be grouped. Alternatively, the method may comprise the step of applying nonlinear factor analysis (NLFA) to the data to identify a plurality of independent components into which the data may be grouped. Also, the method may comprise applying dynamic mathematical modeling to the identified independent components to describe an expression profile for each identified independent component. In an embodiment, the dynamic mathematical modeling comprises a Box-Jenkins approach. In another embodiment, the dynamic mathematical modeling comprises Autoregressive eXogenous (ARX) modeling. In yet another embodiment, the dynamic mathematical modeling comprises Autoregressive (AR) modeling. The method may further comprise the step of applying the nonlinear independent component analysis (NICA) or nonlinear factor analysis (NLFA) in the inverse manner to the expression profile model for an individual component to predict the expression values of an individual gene. In other embodiments, the present invention may comprise systems and computer-readable media for performing the methods of the invention.

Thus, in an embodiment, the method first applies a nonlinear independent component analysis (NICA) to extract the main components that represent the trends of gene expressions. In other embodiments, the analysis may comprise other nonlinear factor analysis (NLFA) techniques. The nonlinear independent component analysis (NICA) or nonlinear factor analysis (NLFA) may be iterative in nature as described herein. For example, in an embodiment, the method comprises a computer-implemented method for analyzing gene expression wherein the method comprises the steps of: (a) compiling data comprising a plurality of measured gene expression signals into a form suitable for computer-based analysis; and (b) analyzing the compiled data using a nonlinear independent component analysis (NICA) or nonlinear factor analysis (NLFA) technique, wherein analyzing comprises identifying an optimum number of independent clusters into which the data may be grouped. In an embodiment, the analysis may comprise a nonlinear factor analysis (NLFA). In another embodiment, the nonlinear independent component analysis is nonlinear independent component analysis.

In an embodiment, the methods and systems of the present invention comprise the use of dynamic mathematical modeling to relate the expression levels of each of the independent components to each other, and to relate genes within each of the independent components to each other and to genes in other groups. The model may be linear or nonlinear. In an embodiment, the modeling comprises a Box-Jenkins Approach. In an embodiment, the modeling comprises autoregressive exogenous (ARX) or autoregressive (AR) modeling. Or, the modeling may comprise moving average modeling.

In yet other embodiments, the computer-implemented method uses an inverse of the nonlinear independent component analysis (NICA) or the nonlinear factor analysis (NLFA) to predict the individual expression values for genes based on the components predicted using the autoregressive method. For example, in an embodiment, an inverse NICA may be used. In certain embodiments, once the values of components in future time step are estimated using dynamic mathematical modeling, such as either AR or ARX modeling, the inverse of the nonlinear component analysis (NICA) model can predict the expression of individual genes in future time steps. The inverse NICA (or NLFA) is simply the straightforward nonlinear mixing of the predicted components for future time steps predicted by dynamic mathematical modeling (e.g., AR or ARX modeling) to form the predicted value of each individual gene in the future time steps.

For example, in an embodiment, the present invention comprises a method to determine the interaction of genes that are involved in the same biological pathway or response. Thus, in an embodiment, the present invention comprises a computer-based method for analyzing gene expression comprising code for: (a) compiling data comprising a plurality of measured gene expression signals into a form suitable for computer-based analysis; (b) using nonlinear independent component analysis (NICA) or nonlinear factor analysis (NLFA) to cluster data comprising a plurality of measured gene expression signals into an optimal number, n, of independent groups, wherein genes in one independent group comprise expression profiles that, on a statistical basis, are substantially independent of the expression profiles for genes in the other groups; and (c) identifying the relation between at least two genes within a cluster group or for genes that are in different groups. An example embodiment comprises a computer-implemented method for analyzing gene expression comprising: (a) compiling data comprising a plurality of measured gene expression signals into a form suitable for computer-based analysis; and (b) analyzing the compiled data using the substeps of: (i) applying a nonlinear independent component analysis (NICA) or nonlinear factor analysis (NLFA) to the data to identify a plurality of independent components into which the data may be grouped; (ii) applying mathematical dynamic modeling to the identified independent components to describe an expression profile for each independent component identified in step (i); and (iii) applying the NICA or NLFA in an inverse manner to the expression profile model for an individual component as derived in step (ii) to predict the expression values of an individual gene. In an embodiment, the nonlinear component analysis is a nonlinear factor analysis. In another embodiment, the nonlinear analysis is a nonlinear independent component analysis. In an embodiment, the dynamic mathematical modeling of step (ii) may comprise a Box-Jenkins approach. In certain embodiments, the dynamic mathematical modeling of step (ii) may comprise autoregressive exogenous (ARX) modeling. In yet other embodiments, the dynamic mathematical modeling of step (ii) may comprise autoregressive exogenous (AR) modeling.

The autoregressive modeling (i.e., AR or ARX) may be used to describe the relationship between genes in different cluster groups, or within a cluster group. In an embodiment, the model provides a numeric relationship among a number of clusters. In an embodiment, if the effects of at least some clusters are disregarded, the model may provide individual coefficients linking pairs of clusters (groups) with mean positive and negative correlations among the pairs. For example, in an embodiment, the autoregressive model may be used to determine if there is a cross-correlation between at least two genes within a cluster group, wherein a positive cross-correlation may comprise the situation in which the expression of one gene in the group is statistically correlated with the expression of a second gene in the same group. For example, for positively correlated genes, the expression of one of the genes may be dependent upon expression of the other gene.

The present invention also comprises computer-readable media which may provide such methods to a plurality of users. Thus, in an embodiment, the invention comprises a computer-readable medium on which is encoded programming code for analyzing gene expression wherein the programming code applies a nonlinear component analysis (NICA) or nonlinear factor analysis (NLFA) to data comprising a plurality of measured signals to identify an optimum number of independent clusters into which the data may be grouped.

A computer-readable medium according to the present invention may include software to evaluate the interaction of genes that are involved in the same biological pathway or response. Thus, in an embodiment, the present invention comprises a computer-readable medium on which is encoded programming code for analyzing gene expression comprising code for: (a) compiling data comprising a plurality of measured gene expression signals into a form suitable for computer-based analysis; (b) using nonlinear independent component analysis (NICA) or nonlinear factor analysis (NLFA) to cluster data comprising a plurality of measured gene expression signals into an optimal number, n, of independent groups, wherein genes in one independent group comprise expression profiles that, on a statistical basis, are substantially independent of the expression profiles for genes in the other groups; and (c) identifying the relation between at least two genes within a cluster group or for genes that are in different groups. An example embodiment comprises a computer readable media comprising code for analyzing gene expression comprising code for: (a) compiling data comprising a plurality of measured gene expression signals into a form suitable for computer-based analysis; and code for (b) analyzing the compiled data using the substeps of: (i) applying a nonlinear independent component analysis (NICA) or nonlinear factor analysis (NLFA) to the data to identify a plurality of independent components into which the data may be grouped; (ii) applying dynamic mathematical modeling to the identified independent components to describe an expression profile for each independent component identified in step (i); and (iii) applying the NICA or NLFA in an inverse manner to the expression profile model for an individual component as derived in step (ii) to predict the expression values of an individual gene. In an embodiment, the dynamic mathematical modeling comprises a Box-Jenkins approach. In another embodiment, the dynamic mathematical modeling comprises autoregressive (AR) or autoregressive exogenous (ARX) modeling. Also, the computer readable medium may also comprise programming code for removing noise from the data, and/or for preparing a report that may be printed on a medium (e.g., computer screen, paper, disk, or for transmission over the internet) for viewing by a user.

Embodiments of the present invention further comprise systems comprising using NICA or NLFA in combination with dynamic mathematical modeling for gene expression array analysis. For example, in an embodiment, the present invention comprises a system for analyzing gene expression using a nonlinear independent component analysis (NICA) or nonlinear factor analysis (NLFA) to identify an optimum number of independent clusters into which data comprising a plurality of measured gene expression signals may be grouped. The system may also comprise using dynamic mathematical modeling to identify the relation between at least two genes within a cluster group or for genes that are in different groups. In alternate embodiments, the dynamic mathematical modeling comprises a Box-Jenkins Approach, autoregressive (AR) modeling, or autoregressive exogenous (ARX) modeling. In yet another embodiment, the system comprises using an inverse of the NICA or NLFA to predict the individual expression values for genes based on the components predicted using the autoregressive method. For example, in an embodiment, the system comprises: a unit for compiling data comprising a plurality of measured gene expression signals into a form suitable for computer-based analysis; and a unit comprising code for using nonlinear independent component analysis (NICA) to cluster data comprising a plurality of measured gene expression signals into an optimal number, n, of independent groups, wherein genes in one independent group comprise expression profiles that, on a statistical basis, are substantially independent of the expression profiles for genes in the other groups, and for identifying the relation between at least two genes within a cluster group or for genes that are in different groups. For example, in one embodiment, the system may comprise: (a) a unit for compiling data into a form suitable for computer-based analysis, wherein the data comprises a plurality of measured gene expression signals from the at least one cell type; (b) programming code for analyzing the compiled data comprising the substeps of: (i) applying a nonlinear independent component analysis (NICA) or nonlinear factor analysis (NLFA) to the data to identify a plurality of independent components into which the data may be grouped; (ii) applying dynamic mathematical modeling to the identified independent components to describe an expression profile for each independent component identified in step (i); and (iii) applying the NICA or NLFA in an inverse manner to the expression profile model for an individual component as derived in step (ii) to predict the expression values of an individual gene; and (c) a unit for transmitting the results of said analysis to a user. In an embodiment, the dynamic mathematical modeling of step (ii) comprises a Box-Jenkins approach. In other embodiments, the dynamic mathematical modeling may comprise autoregressive (AR) or autoregressive exogenous (ARX) modeling. Also, the system may comprise programming code for removing noise from the data and for preparing a report that may be printed on a medium (e.g., computer screen, paper, disk, or for transmission over the internet) for viewing by a user.

In certain embodiments, the methods, systems, and computer readable media provide an analysis of gene expression based on nonlinear independent factor analysis (e.g. NICA or NLFA) model, and an autoregressive exogenous model (ARX) such as the models below:

$$x(t)=g(s(t))+n(t)=B \tan h(As(t)+a)+b+n(t) \quad \text{(NICA/NLFA)}$$

where: $s(t)=(y_1(t), y_2(t), y_3(t), \ldots y_p(t))$ with $y_i(t)$ representing the expression level of the independent component i, and:

$$y_i(t)=f(y_1(t), y_2(t) \ldots y_p(t), u_1(t), u_2(t) \ldots u_M(t))+e(t) \quad \text{(ARX)}$$

where; $u_1, u_2 \ldots u_M$, corresponds to the environmental factors 1, 2 . . . M, and experimental noise is defined by e In yet another embodiment, the present invention comprises an isolated nucleic acid molecule comprising a sequence having a gene expression profile and/or gene function as identified using nonlinear independent component analysis in combination with dynamic mathematical modeling (e.g., AR, ARX, or Box Jenkins modeling). In an embodiment, the isolated nucleic acid sequence may comprise DNA. In another embodiment, the nucleic acid may comprise RNA. In an embodiment, the nucleic acid may comprise double-stranded DNA. Alternatively, the isolated nucleic acid may comprise single-stranded DNA. In an embodiment, the nucleic acid may comprise single-stranded RNA. Alternatively, the nucleic acid may comprise a double-stranded RNA or an RNA molecule comprising a double-stranded region. In yet another embodiment, the nucleic acid may comprise a RNA-DNA hybrid.

For example, in an embodiment, the isolated nucleic acid may comprise a genomic DNA sequence. The genomic DNA may be full-length, or may correspond to a partial gene sequence. In another embodiment, the isolated nucleic acid sequences may comprise a full-length or partial cDNA sequence. In another embodiment, the isolated DNA may comprise a short oligonucleotide.

In yet another embodiment, the isolated nucleic acid may comprise a RNA sequence. The RNA may comprise a full-length mRNA. Alternatively, the RNA may comprise a small inhibitory RNA which may be used to inhibit gene expression.

In an embodiment, the number of groups identified using the methods and systems of the present invention is correlated to the pattern of gene expression. In an embodiment, the plurality of data points comprise an array of DNA sequences hybridized to mRNA. The array of DNA sequences may comprise a solid-state array. For example, the data may comprise an array of DNA sequences of known identity hybridized to mRNA isolated from cells that are treated with a pharmaceutical agent over a period of time. Isolation of mRNA from the cells at various time points, and hybridization of the mRNA to the DNA array, can identify genes that may have changed expression profiles in response to the pharmaceutical agent. The present invention provides statistical tools for analyzing the thousands of data points that may result from such an experiment.

Thus, in an embodiment, the plurality of measured signals comprise hybridization data for a plurality of known gene sequences. Also, in an embodiment, the number of independent clusters identified by nonlinear component analysis is correlated to the pattern of gene expression for the at least one cell type.

As described herein, the methods, products, and systems of the present invention provide for the development of mathematical models to explain gene expression profiles and how the expression of one gene may relate to the expression of a second gene. Also, the methods, products, and systems of the present invention provide for the development of mathematical models to explain gene expression profiles and how the expression of one gene, or several genes in a pathway may change over time. In yet another embodiment, the mathematical modeling can be used to predict the expression profile for individual genes for which data in the past and/or the future has been modeled (e.g., to predict the values of individual genes in the middle of a gene expression time series). Thus, in an embodiment, the autoregressive (AR) model or autoregressive exogenous (ARX) model is used to predict the levels of expression of individual genes over time. In an embodiment, the AR or ARX model applies data derived from a subset of the time points for which data is available and uses that subset of data to predict gene expression over a larger period of time. For example, in an embodiment, the AR or ARX model that describes the gene expression profile for the various independent gene clusters (i.e., independent components) is derived using data derived from a subset of data derived from the earliest time points for which data is available.

In an embodiment, the methods, products and software of the present invention correlate at least one of the measured signals, x, to the underlying source(s), s, generating the signal, and experimental noise, n. In an embodiment, the methods, products and systems of the present invention correlate at least one of the measured signals, x, to the underlying sources, s, generating the signal, and experimental noise, n, as a function of time, t, such that: $x(t) = f(s(t)) + n(t))$, where $n(t)$ is additive noise, and $f(.)$ describes the nonlinear mapping (mixtures). In one embodiment, $x(t) = [x_1(t), x_2(t), \ldots x_K(t)]$ and $s(t) = [y_1(t), y_2(t), \ldots y_P(t)]$, where $x_i(t)$ represents the expression level of gene i at time t and $y_j(t)$ denotes the value of the jth component at time t.

In an embodiment, a multilayer perceptron (MLP) network may be used to model the nonlinearity of the system. In an MLP network, the sources are on the top layer and observations are on the bottom layer. The middle layer consists of hidden neurons each of which computes a nonlinear function of the inputs. The MLP network can be used to model many naturally occurring multidimensional nonlinear processes. For example, in many cases MLP may provide a simpler parameterization for the involved nonlinearity than Taylor or Fourier series explanations. The equation of MLP mapping is:

$$x(t) = f(y(t)) + n(t) = B \tan h(As(t) + a) + b + n(t) \tag{1a}$$

where the matrices A and B are the weights of the first and second layers, and vectors a and b are the corresponding bias terms.

In certain embodiments of the methods, systems and products of the present invention, the method of nonlinear independent component analysis comprises using a neural network defined as: $x(t) = g(s(t)) + n(t) = B \tan h(As(t) + a) + b + n(t)$, wherein the neural network is used in combination with back propagation to model the nonlinearity of the system such that A, B, a and b are determined for the data set. The main goal of "learning" or "training the model" (i.e., finding the optimal values of A, B, a and b) is to approximate the posterior probability distribution function (PDF) of all the unknown values in the model, by minimizing a cost function defined based on posterior PDFs. The details of minimizing the cost function can be found in Hartemink et al., 2002, *Pac. Symp. Biocomput.*, 437-439. The values of NICA model A, B, a, and b may be determined using a back propagation algorithm as is known in the art (Lappalainen, H. and Honkela, A., Bayesian Nonlinear Independent Component Analysis by Multi-Layer Perceptrons, In *Advances in Independent Component Analysis*, ed., Mark Girolami, Springer, pp. 93-121, 2000). After obtaining the optimal set of parameters A, B, a, and b, the sources can be estimated by training the neural network using methods known in the art. The algorithm is a reversible process because after applying any change on the sources the new observation can be reconstructed by the network.

For example, in one embodiment, since in nonlinear factor analysis, the factors are assumed to have Gaussian distribution, Gaussian distribution would be a fair approximation for the posterior probability density of the unknown variables. In addition, the variances of the Gaussian distributions of parameters of the model are parameterized by logarithm of standard deviation, i.e. log-std. This is done because the posterior distribution of these parameters will be then closer to Gaussian which agrees better with the assumption that the posterior is Gaussian. The noise n(t) is assumed to be independent and Gaussian, therefore:

$$x(t) \sim N(f(y(t), e^{2v_x}) \tag{1b}$$

Each component of the vector $v_x$ gives the log-std of the corresponding component of x(t). The sources are assumed to have zero mean Gaussian distributions and again the variances are parameterized by log-std $v_y$.

$$y(t) \sim N(0, e^{2v_y}) \tag{1c}$$

The main objective of ensemble learning is to approximate the posterior pdf of all unknown variables in the model. This means that from the observations x(t), an estimate the statistical properties of all unknown values of the model including the sources and parameters, denoted as $\xi$ is performed. For this, a cost function may be defined as the misfit between the actual posterior pdf $p(\zeta|x)$ and its approximation $q(\zeta|x)$. The posterior can then be approximated as a product of independent Gaussian distributions:

$$q(\zeta|x) = \prod_i q(\zeta_i|x) \tag{1d}$$

For each individual Gaussian distribution the posterior mean $\bar{\zeta}$ and variance $\tilde{\zeta}$ may be used. The cost function $C_\zeta(x; \bar{\zeta}, \tilde{\zeta})$ can be defined between actual posterior $p(\zeta|x)$ and its factorial approximation $q((\zeta|x)$. The functional form of cost function can be found in (Lappalainen et al., 2000). The optimization of cost function would be done with respect to posterior mean $\bar{\zeta}$ and posterior variance $\tilde{\zeta}$. The details of optimization technique have been described in (Lappalainen et al., 2000). The updating of A, a, B, and b, according to the backpropagation algorithm is controlled according to an iterative process that improves the existing values of these parameters to improve the overall error.

After optimization, the estimates of all source (factor or trend) signals as well as parameters of the network are available. This allows us to feed the estimated factor signals to an ARX model that relates the present values of factors to their past values.

In an embodiment, the technique is applied to obtain major trends which then represent "clusters" or "state variables" (i.e., prototypes of the clusters or independent components) facilitating the estimation of the expression values for all genes. So the expression value of all genes in a specific number of time steps plays the role observations in nonlinear components analysis technique and the major trends of the genes are the sources.

In an embodiment, the plurality of measured signals correspond to hybridization data used to measure the expression of a gene or a plurality of genes. For example, in an embodiment, the plurality of measured signals comprise a plurality of known DNA sequences hybridized to mRNA isolated from the at least one cell type. In an embodiment, the plurality of known DNA sequences are arranged to form a solid-state array. For example, microarrays such as those commercially available from Affymetrix (Santa Clara, Calif.) may be used.

The method provides the statistical tools to analyze the large number of data points generated in gene expression array hybridization experiments. In an embodiment, the number of data points analyzed using the methods, software products, and systems of the present invention is greater than 100 per single analysis. In other embodiments, the number of data points may be greater than 1,000 per single analysis, or greater than 10,000 data points per single analysis.

In an embodiment, raw data may be suitable for the algorithms of the invention. In some cases, however, it may be preferred to transform the data in some manner. For example, in an embodiment, the data may be transformed to describe the logarithm of the ratio of two signals, $y_i(t)=\log_2(R_i(t)/G_i(t))$, where R and G represent the measured signal for gene i measured under two different experimental conditions, over time, t. In an embodiment, R may correspond to gene expression for control cells and G may correspond to gene expression for experimental cells.

The computer-implemented methods, products, and systems of the present invention may utilize an iterative analysis to describe an optimal number of independent gene groups that explain the gene expression profiles being measured. In an embodiment, the number of gene groups, n, is estimated as a preset number, $n_0$. The data may then be evaluated by increasing the number of groups from $n_0$ and performing an iterative analysis of the relative fit of the data using $n_0$ as compared to the new value of n. In an embodiment, the number of groups are increased incrementally by 1 group for each evaluation, such that the number of groups increases at each step from $n_0$, to $n_0+1$, to $n_0+2$, until the optimum number of groups ($n_{opt}$) is determined.

Thus, in an embodiment, the method may be designed such that the fit of the data to a certain number of independent gene groups may be evaluated during the course of the analysis, thus identifying the number of independent gene groups that best explains the data. The evaluation of the fit of the data to the current number, n, of independent gene groups may be performed at each iteration, or after several iterations (e.g., after 3 successive iterations, or the like).

In an embodiment, evaluation of the data fit may include the step of maximizing the mutual information within each of the resulting clusters or independent gene groups. Also, the evaluation of the data fit may comprise minimizing the mutual information outside of the resulting clusters or independent gene groups. Also, the evaluation of the data fit may comprise maximizing the information distance across clusters or hyper-volume outside of the resulting clusters or gene groups. The evaluation of the fit of the data to certain number of independent clusters may also comprise minimizing the information distance or hyper-volume within each of the resulting clusters or gene groups. As yet another level of analysis, the method may comprise using an independent method to analyzing the identified independent components for biological relevance. For example, in an embodiment, the expression profiles for known genes may be evaluated to determine if they are relevant to the biological function under study.

In an embodiment, the algorithm used for grouping the genes into clusters is designed to reduce or minimize computational memory required for matrix analysis. For example, for NICA, programs such as an unofficial nonlinear factor analysis Matlab package created by Laboratory of Computer and Information Science, Adaptive Informatics Research Center at Department of Computer Science and Engineering at the Helsinki University of Technology (available on line at the Helsinki University of Technology website) may be used.

Or, the analysis may comprise hierarchical ICA such that the complexity of the computational analysis is reduced as the analysis proceeds by removing data inputs that have been described at earlier stages of the analysis from the set of data points still remaining to be characterized. Also, several commercially available ICA algorithms known to provide efficient analysis, with significantly reduced memory demands may be used. In an embodiment, efficient ICA algorithms may not be as accurate as standard ICA algorithms. Thus, an assessment of the ability of the algorithm to provide the analysis required may be performed using test data prior to utilizing a particular algorithm for the analysis or part of the analysis.

As with most statistical packages, the present invention may comprise removing signal due to noise from the data. Noise may be removed by a variety of methods known in the art including, but not limited to, filtering signals that are less than a pre-determined level. In another embodiment, removing noise may comprise the step of normalizing the variance of the data. For example, in an embodiment, normalization around the mean, median, start point, or end point may be performed.

Once the genes have been clustered into meaningful groups, the methods, products and systems of the present invention may utilize dynamic mathematical modeling to relate the expression levels of each of the genes in the cluster pool to each other or to gene in other clusters. The model may be linear or nonlinear. In certain embodiments, the modeling comprises autoregressive (AR) or autoregressive exogenous (ARX) modeling. Or, the modeling may comprise moving average modeling. In yet another embodiment, the modeling may comprise a Box-Jenkins Approach.

In an embodiment, autoregressive modeling is applied to relate the expression levels of each of the prototypes in all gene clusters to each other. The model may relate the future expression level of the prototypes of gene clusters ($y_i$'s) to the values of other prototypes in past time(s). In an embodiment, the model also considers the uncertainty inherent to the model by considering a noise factor.

In an embodiment, the methods, systems and products of the present invention further allows for determining the interaction of genes within a gene group. In this way, the interrelationship of individual genes within a particular group of genes may be described. For example, the cross-correlation between genes within a group may be determined, wherein a positive cross-correlation comprises the situation in which the expression of one gene in the group is statistically correlated with the expression of a second gene in the same group. For example, the expression of one of the genes may be dependent upon expression of the other gene thereby resulting in a positive cross-correlation. Or, the analysis may describe which genes are activated in response to a particular environmental stimulus or pharmaceutical agent.

In an embodiment, the relationship between genes within a group is expressed as a mathematical model describing relative levels of gene expression for at least two of the genes in the group. It is understood that gene expression does not occur in isolation and thus, may be influenced by, or reflect the contribution of, a variety of extraneous factors. For example, in an embodiment, the mathematical model describes expression of genes $y_1, y_2 \ldots y_P$, in a group may include the contribution of at least one environmental factor. Or, the model may include the contribution of time. The model may also include the contribution of noise. For example, in an embodiment, the model comprises the expression $y_i = f(y_1, y_2, \ldots y_P, u_1, u_2, \ldots u_M) + e$, where $y_1, y_2 \ldots y_P$, is the expression of gene groups 1, 2, . . . P; $u_1, u_2 \ldots u_M$ corresponds to environmental factors 1, 2 . . . M, and experimental noise is defined by e.

In some cases the mathematical model may be simplified such that the underlying physiological process is better revealed. For example, in an embodiment, contributions of extraneous factors and/or noise may be approximated using a simple function. Also in an embodiment, statistically weak links may be removed from the model. Finally, the model may be evaluated in light of test data to determine whether particular pathways are required to understand the phenomenon of interest.

As described herein, the present invention may comprise systems using the computer-readable medium comprising nonlinear independent component analysis (NICA) or nonlinear factor analysis (NLFA) for gene expression array analysis. Thus, as described above, the present invention comprises a system for analyzing gene expression comprising using nonlinear independent component analysis (NICA) or nonlinear factor analysis (NLFA) to identify an optimum number of independent clusters into which data comprising a plurality of measured signals may be grouped and then applying dynamic mathematical modeling (e.g., autoregressive modeling or autoregressive exogenous modeling) to describe the behavior of the cluster or group. In an embodiment, the system comprises a computer and programming code embodied on a computer-readable medium.

The system may comprise an imaging unit as well as a means for the user to interact with the system as the analysis proceeds. Thus, in an embodiment, the present invention further comprises a unit for collecting and/or compiling data from said plurality of measured signals and transmitting said data to said computer, and a unit for transmitting the results of said analysis to a user.

In an embodiment, the systems of the present invention are designed for high-throughput analysis of DNA hybridization data. Thus, in an embodiment, the plurality of measured signals comprise a plurality of known DNA sequences hybridized to mRNA isolated from at least one cell type.

In an embodiment, the system utilizes an iterative analysis to provide an optimal number of independent gene groups that explain the gene expression profiles being measured. In an embodiment, the number of gene groups, n, is estimated as a preset number, $n_0$. The data may then be evaluated by increasing the number of groups from $n_0$ and performing an iterative analysis of the relative fit of the data using $n_0$ as compared to the new value of n. In an embodiment, the number of groups are increased incrementally by 1 group for each evaluation, such that the number of groups increases at each step from $n_0$, to $n_0+1$, to $n_0+2$, until the optimum number of groups ($n_{opt}$) is determined. Also, in an embodiment, the system comprises hierarchical nonlinear component analysis such that the complexity of the computational analysis is reduced as the analysis proceeds, by removing inputs that have been described at earlier stages of the analysis from the set of data points still remaining to be characterized.

Once the genes have been clustered into meaningful groups, dynamic mathematical modeling may be used to model the behavior of the groups. In an embodiment, autoregressive (AR) or autoregressive exogenous (ARX) modeling may be applied to relate the expression levels of each of the prototypes in all gene clusters to each other or to genes in other groups. The model may relate the future expression level of the prototypes of gene clusters ($y_i$'s) to the values of other prototypes in past time(s). In an embodiment, the model also considers the uncertainty inherent to the model by considering a noise factor. In an embodiment, the present invention further allows for determining the interaction of genes within a gene group. In this way, the interrelationship of individual genes within a particular group of genes is described. For example, the cross-correlation between genes within a group may be determined, wherein a positive cross-correlation comprises the situation in which the expression of one gene in the group is statistically correlated with the expression of a second gene in the same group.

In an embodiment, the system employs software to describe the relationship between genes within a group as a mathematical model describing relative levels of gene expression for at least two of the genes in the group. In an embodiment, the mathematical model describes expression of genes $y_1, y_2 \ldots y_P$, in a group may include the contribution of at least one environmental factor. Or, the model may include the contribution of time. The model may also include the contribution of noise. For example, in an embodiment, the model comprises the expression $y_i = f(y_1, y_2, \ldots y_P, u_1, u_2, \ldots u_M) + e$, where $y_1, y_2 \ldots y_P$, is the expression of gene groups 1, 2, . . . P; $u_1, u_2 \ldots u_M$ corresponds to environmental factors 1, 2 . . . M, and experimental noise is defined by e.

In an embodiment, the autoregressive (AR) or autoregressive exogenous (ARX) model is used to predict the levels of expression of individual genes over time. In an embodiment, the autoregressive model applies data derived from a subset of the time points for which data is available and uses that subset of data to predict gene expression over a larger period of time. For example, in an embodiment, the AR or ARX model that describes the gene expression profile for the various independent gene clusters (i.e., independent components) is derived using data derived from a subset of data derived from the earliest time points for which data is available.

Gene Array Analysis

DNA microarrays are essentially solid-state grids containing short sequences of DNA of known sequence fixed at a particular position (or address) on the grid (Bassett, D. E., et al., *Nature Genetics*, 21:51-55, 1999; Hughes T. R., et al., *Curr. Opin. Chem. Biol., February;* 5:21-5, 2001; Harkin D. P., *Oncologist*, 5:501-7, 2000; Southern, E., et al., *Nature*

*Genetics,* 21: 5-9, 1999; Greenberg S. A., *Neurology,* 57:755-61, 2001; Schulze A., *Nat. Cell. Biol.,* 3:E190-5, 2001; Bowtell, D. D., *Nature Genetics,* 21:25-32, 1999; Devaux, F., et al., *FEBS. Lett.,* 498:140-4, 2001; Cheung, V. G., et al., *Nature Genetics,* 21:15-19, 1999; Blohm, D. H., et al., *Curr. Opin. Biotechnol.,* 12:41-7, 2001; Hegde P., et al., *Biotechniques, September;* 29(3):548-50, 2000, Duggan, D. J., et al., *Nature Genetics,* 21:10-14, 1999, Hacia, J. G., *Nature Genetics,* 21:42-47, 1999. In some cases, the DNA sequences are short fragments of DNA generated from a library. Alternatively, some arrays comprise oligonucleotide sequences (short fragments of DNA less than 50 nucleotides long) each of which may only differ by one base pair (commercially available from AFFYMETRIX®, Santa Clara, Calif.).

Regardless of how the array is formulated, DNA microarrays may be used to identify genes expressed in the cell. When mRNA isolated from a cell is hybridized to a DNA array, the DNA sequences complementary to the expressed mRNA will exhibit hybridization. The mRNA may be tagged (e.g., with a fluorescent label or a radiolabel) so that hybridization can be detected as a spot (or signal) at a particular address on the array. Once the address is determined, the DNA sequence complementary to the gene being expressed may be used to identify the mRNA product and thus, the gene encoding the mRNA.

To detect changes in gene expression, the cell may be perturbed, as for example, by adding a drug or changing the environmental conditions, and isolating mRNA from the perturbed cells. The mRNA may then be labeled (or tagged) as described above and hybridized to the array. By controlling the hybridization conditions, the signal generated by the tagged mRNA is proportional to the mRNA in the sample. Thus, the image of the microarray upon hybridization of the tagged mRNA will identify those genes that have changes in expression relative to the array probed with mRNA from a control cell. In many cases, it is the change over time which is of interest and so, a microarray will be analyzed by hybridizing the array to mRNA isolated at varying time points after or during perturbation of the cell of interest. With each array having thousands of unique DNA sequences each at a unique address, correlating gene expression measured as hybridization to one or several microarrays can be a daunting task.

A. Grouping Related Genes

Many techniques have been applied to the problem of making sense of large amounts of gene expression data. Cluster analysis techniques (e.g., K-Means), self-organizing maps (SOM), principal components analysis (PCA), and other analysis techniques are all widely available in packaged software used in correlating this type of gene expression data.

Cluster analysis is a loose term covering many different algorithms for grouping data. Clustering can be divided into two main types: top-down and bottom-up. Top-down clustering starts with a given number of clusters or classes and proceeds to partition the data into these classes. Bottom-up clustering starts by grouping data at the lowest level and builds larger groups by bringing the smaller groups together at the next highest level.

K-Means is an example of top-down clustering. K-means groups data into K number of best-fit clusters. Before using the algorithm, the user defines the number of clusters that are to be used to classify the data (K clusters). The algorithm randomly assigns centers to each cluster and then partitions the nearest data into clusters with those centers. The algorithm then iteratively finds new centers by averaging over the data in the cluster and reassigning data to new clusters as the centers change. The analysis iteratively continues until the centers no longer move (Sherlock, G., *Current Opinion in Immunology,* 12:201, 2000).

Tree clustering is an example of bottom-up clustering. Tree clustering joins data together by assigning nearest pairs as leaves on the tree. When all pairs have been assigned (often according to either information-theoretical criteria or regression methods), the algorithm progresses up to the next level joining the two nearest groups from the prior level as one group. Thus, the number and size of the clusters depends on the level. Often, the fewer clusters, the larger each cluster will be. The stoppage criteria for such algorithms varies, but often is determined by an analysis of the similarity of the members inside the cluster compared to the difference across the clusters.

Self-organizing maps (SOMs) are competitive neural networks that group input data into nearest neighbors (Torkkola, K., et al., *Information Sciences,* 139:79, 2001; Toronen, P., et al., *FEBS Letters,* 451:142-146, 1999). As data is presented to the neural network, neurons whose weights currently are capable of capturing that data (the winner neuron) are updated toward the input. Updating the weights, or training the neural net, shifts the recognition space of each neuron toward a center of similar data. SOMs are similar to K-means with the added constraint that all centers are on a 1 or 2 dimensional manifold (i.e., the feature space is mapped into a 1 or 2 dimensional array, where new neighborhoods are formed). In SOM, the number of neurons is chosen to be much larger than the possible number of the clusters. It is hoped that the clusters of trained neurons will provide a good estimation of the number of the neurons. In many cases, however, a number of small clusters are formed around the larger clusters, and there is no practical way of distinguishing such smaller clusters from, or of merging them into, the larger clusters. In addition, there is no guarantee that the resulting clusters of genes actually exhibit statistically independent expression profiles. Thus, the members of two different clusters may exhibit similar patterns of gene expression.

Principal component analysis (PCA), although not a clustering technique in its nature (Jolliffe, I. T., Principal Component Analysis, New York: Springer-Verlag, 1986) can also be used for clustering (Yeung, K. Y., et al., *Bioinformatics,* 17:763, 2001). PCA is a stepwise analysis that attempts to create a new component axis at each step that contains most of the variation seen for the data. Thus, the first component explains the first most important basis for the variation in the data, the second component explains the second most important basis for the variation in the data, the third component the third most important basis, and so on. PCA projects the data into a new space spanned by the principal components. Each successive principal component is selected to be orthogonal to the previous ones, and to capture the maximum information that is not already present in the previous components. The principal components are therefore linear combinations (or eigenarrays) of the original data. These principal components are the classes of data in the new coordinate generated by PCA. If the data is highly non-correlated, then the number of significant principal components can be as high as the number of original data values. If, as in the case of DNA microarray experiments, the data is expected to correlate among groups, than the data should be described by a set of components which is fewer than the full complement of data points. PCA is a highly efficient dimension-reduction technique. One of the disadvantages of PCA, however, is that the resulting coordinates often have no physical meaning. Thus, it is often not possible to extract rules and patterns from the resulting clusters. Another disadvantage is that PCA assumes that the clusters are orthogonal (perpendicular) to each other; in reality, this is often not the case.

In many cases, these techniques cannot accurately describe the true number of gene groups. For array analysis, the analysis may provide vastly different results depending upon how many independent gene groups are assumed. Thus, inaccurate clustering analysis can skew the data such that results of further analyses are compromised.

Another disadvantage of the existing microarray processing technologies is the lack of a reliable method for eliminating signals due to noise. Microarray measurements are hybridization-based and thus, the location and/or intensity of a signal may vary with experimental conditions. Also, some genes have high variance in their expression profiles. In some cases, genes with noisy expression profiles unrelated to the physiological process under study can complicate the clustering techniques and result in too many clusters. Finally, noise may result from the misidentification of samples or other human error.

Modeling of the regulatory networks may allows quantitative estimation of gene expression, which in turn facilitates and expedites studies such as drug discovery. In recent years several methods have been introduced to address this problem. These methods include Boolean Networks (Eisen et al., Proc. Natl. Acad. Sci., U.S.A. 95:14863-14868, 1998), Bayesian Networks (Kauffman, 1993; Arkin et al., 1998), Dynamic Bayesian Networks (Gat-Viks et al., 2003), linear models (Yuh et al., 1998), compartment modeling using differential equations (Akutsu et al, 1999), techniques based on control theory (Kholodenko et al., 2002), full biochemical interaction models (Yeung et al., 2002) and methods using metabolic regulation concepts (Somogyi et al., 1997;). While some of these techniques such as Boolean networks can be abstract and overly simplified, others are computationally extremely complex. Some of the more complex models may include techniques modeling all biochemical interactions among genes based on a large number of differential equations.

In many drug discovery applications, while knowing the steady-state effects of drug is vital, the drug's short-term activities and potential transient effects on the molecular level must also be thoroughly studied and analyzed. As a result, inferring dynamic gene regulatory networks that can be extracted from time series DNA microarray data can important.

Such analyses may employ an autoregressive (AR) or an autoregressive exogenous (ARX) model. In a typical AR or ARX models, the main variables, for example, the expression profile for individual genes, are considered as variables of the AR or ARX model, and the values of these variables for the future time samples are estimated using the model.

In direct modeling of the interactions among a large number of genes with AR or ARX models, an extremely large number of training points (in time) may be required to reliably estimate all model coefficients. The number of genes involved in a biological process may be so large that it can be extraordinarily difficult to develop reliable AR or ARX models directly from the data by incorporating all of the genes as variables in the model. Nor does a blind application of AR or ARX models to molecular biology problems provide insightful clustering of the genes involved in a biological process, as such models tend to fail to display the massive grouping and parallelism that may be present in a genetic network. The present invention employs a unique method to handle a large number of variables (i.e., genes) for analysis by AR or ARX modeling.

The methods and systems of the present invention recognize the difficulty of AR and/or ARX modeling large numbers of data, by exploiting the fact that related genes may behave very similarly in a biological process, and therefore the role and effects of these genes can be somehow combined by a suitable clustering technique before dynamic modeling. For example, for some types of modeling, the clustering technique may be linear as described in some of the experiments herein. Generally, however, the clustering provided by nonlinear methods provides a more accurate fit of the data as compared to clustering using linear models. In an embodiment, clustering significantly reduces the parameters of the AR or ARX model. The use of either linear ICA or NICA provides significant improvement over other clustering techniques such as K-means, Tree clustering, Self-organizing maps, or linear PCA. For example, a disadvantage of linear PCA clustering, is that it may only find the model between prototypes of different classes of genes, and therefore, may not predict the expression value of individual genes with high accuracy.

The present invention is distinct from previous microarray analysis techniques in that it employs a nonlinear clustering techniques, such as independent component analysis (NICA) or nonlinear factor analysis (NLFA), as a means to determine the optimal number of independent gene groups (i.e., clusters) that best explains the data, in combination with dynamic mathematical modeling (e.g., AR or ARX) to define the interrelationships between various genes within gene groups or in different gene groups. Thus, embodiments of the present invention comprise methods and systems that efficiently address the analysis of gene array data to identify independent clusters of gene expression profiles and to describe and quantify interrelated pathways for genes within a cluster and between clusters.

In an embodiment the method first applies nonlinear independent component analysis (NICA) to extract the main components that represent the trends of gene expressions. The method may then employ an Autoregressive (AR) or Autoregressive eXogenous (ARX) modeling to define the interactions among these components. Next, an inverse application of the nonlinear independent component analysis (NICA) may be used to predict the individual expression values for genes based on the components predicted using the autoregressive method. In an embodiment, once the values of components in future time step are estimated using the AR or ARX model, the inverse of the nonlinear independent component analysis (NICA) model can predict the expression of individual genes in future time steps.

An overview of the method (2) is shown in FIG. 1. A nonlinear independent component analysis (e.g., NICA) may be used to group related genes into clusters (4). For example, where the expression profile is measured over time, the nonlinear components analysis may used to extract the major time components of all genes from gene expression data (3). In an embodiment, the genes are isolated from cells or tissues that have been exposed to a drug or other treatment of interest. Next, Autoregressive eXogenous (ARX) modeling may be applied to the groups to model the interactions among all of the genes (6) and the effect of environmental stimuli (e.g., drugs, chemicals, etc) (7). Based on the model derived, an inverse application of the nonlinear independent component analysis (NICA) may be used to predict gene expression profiles for individual genes for subsequent time steps (8). Thus, in a embodiment, applying ARX on a few components as opposed to a large number of genes dramatically reduces the number of model parameters and results to a much more reliable model. Once these two steps are performed, the ARX model can predict the future values of the components. Then using these predicted values for the components and the NICA formulation in the inverse form, one can predict the future values of individual genes.

In one example embodiment, NICA is used to cluster genes into groups. Although computationally intensive, NICA is particularly suited for cluster analysis. NICA decomposes an input dataset into components so that each component is as statistically independent from the others as possible. Thus, in NICA, data is clustered such that the correlation for individuals within a group is maximized (i.e., intra-group samples are highly correlated), while the correlation for individuals in separate groups is minimized (i.e., samples in different groups show minimal correlation).

ICA (linear and/or nonlinear) is commonly applied to blind source separation (BSS). An example of BSS often used portray ICA is the cocktail party problem. At a cocktail party, an individual in one group has to be able to concentrate on one set of audio signals amongst the din of audio signals from several other groups. Assuming that each group is talking about issues that are unrelated to each other, an individual in the first group is usually capable of following the conversation in their own group and separating that conversation from those of other groups. The blind separation of a rather small number of signals from independent sources may be a rather easy task for the human brain, but it is an extremely difficult task for a computer—especially when the number of interfering signals is very large. ICA has been used for discerning underlying patterns in a set of signals, such as electroencephalographic (EEG) signals (Makeig, S., et al., *Proceeding of the Advances in Neural Information Processing Systems*, Eds., Touretzky et al., MIT Press, pp. 145-151, 1996; Vigario, R., et al., *Electroenceph. Clin. Neurophysiol.*, 103:395-404, 1997), magnetic resonance imaging (MRI) signals (Stone, J. V. et al., *NeuroImage*, 15:407-421, 2002), and even financial data (Back, A. D., et al., *Int. J. Neural Syst.*, 8:473-484, 1997).

In the microarray problem, the true objective is to identify groups of genes that that are activated and/or suppressed in response to certain biological changes or signals. Unlike PCA, ICA can take higher order statistics into account, and can utilize non-orthogonal transformation. Because ICA is capable of identifying groups of entities with highly similar statistical characteristics, ICA is highly suitable for microarray processing. Once the independent groups of genes are identified, the correlation, and in some cases the causality, of gene expression among these gene groups can be explored more effectively.

Linear ICA has recently been applied to microarray analysis. For example, it has been shown that as compared to PCA, ICA can be superior in clustering yeast genes in such a manner as to mirror known expression profiles (Hori, G., et al., Blind gene classification on ICA of microarray data, ICA 2001 meeting, SanDiego, U.S.A., pp. 332-336). Also, Lee and Batzogou (Lee, S.-I. et al., *Genome Biology*, 4:R76, October 2003) describe the use of ICA to fit microarray data to a predetermined number of gene expression groups. Both of these studies, however, pre-specified the number of clusters (i.e., gene groups) into which the data should be fit. In contrast, the methods of the present invention do not require a pre-specified number of clusters but finds the optimal number of clusters automatically. Also, and as described herein, the methods of the present invention have the ability to incorporate the dynamics and convolution of signals in time into the analysis.

The fundamental equation for ICA is as follows.

$$x(t)=g(s(t))+n(t) \tag{1}$$

In an embodiment, $s(t)=(y_1(1), y_2(t), \ldots y_P(t))^T$, represents the underlying sources, $n(t)=(n_1(t), n_2(t), \ldots n_M(t))^T$, represents the noise in the system, $x(t)$ represents the experimentally measured signals, "T" defines the transpose operation, and $f$ is a function that mixes the sources. From this fundamental equation many specialized techniques have been developed. For example, a linear mixing model would replace equation (1) with equation (2)

$$x(t)=As(t)+n(t) \tag{2}$$

where A is the mixing matrix.

Classical ICA is a linear mixing model that ignores the noise term and gives the simple relation shown in equation (3).

$$x(t)=As(t) \tag{3}$$

Linear ICA may also be used for grouping genes into clusters. In linear ICA, determination of the relationship between the expression of genes and/or gene clusters and the biological processes requires estimation of, W, the inverse of the matrix A (i.e., $W=A^{-1}$) to reconstruct s from x. The goal of linear ICA is to estimate W (de-mixing matrix) to thereby estimate the sources, s, from the measured expression levels, x. This may be done using static ICA (e.g., Lee and Batzoglou, 2003) or other types of ICA.

For example, the equation used to iteratively estimate W(new) (the next updated value of matrix W) based on W(old) (the present value of matrix W) is:

$$W(\text{new}) = W(\text{old}) - \frac{[E\{xg(W(\text{old})^T x)\} - \alpha W(\text{old})]}{[E\{g(W(\text{old})^T x)\} - \alpha]}$$

where: E[.] represents a statistical expectation function, $\alpha$ is a parameter controlling the rate of convergence, and g(.) is a sigmoid function. For example, in an embodiment, a choice of sigmoid function g is:

$$g(r)=\tan h(cr) \tag{5}$$

where c is a constant, and r is the variable. Other sigmoid functions such as $\tan^{-1}(.)$, may also be used.

There are many other versions of ICA, however, that are each specialized for a particular functionality and that may be used with the methods of the present invention. For example, ICA may be used to model a cell having M independent biological processes forming an M-dimensional time-series, s(t). For example, a set of biological processes of interest may be monitored by microarray analysis as the time variation in gene expression of N genes where the interaction among M biological processes and the expression of N genes may be represented as an N-dimensional microarray expression time-series x(t). In this way, the system may be analyzed using ICA that attempts to recover unknown s(t) from measured x(t).

For example, it may be assumed that $y_i(t)$ is the gene expression of gene i through time steps t=1, 2, . . . , k, where k is the number of time steps. Now, assume that N is the number of genes passing through the filtering stage, P is the degree of the dynamics the system (i.e., the maximum delay in time for which the previous expressions can still affect the expression levels in the present time). One may define the time-dependent matrix x(t) as follows.

$$x(t) = \begin{bmatrix} y_1(t) \\ y_1(t-1) \\ y_1(t-2) \\ \vdots \\ y_1(t-P) \\ y_2(t) \\ y_2(t-1) \\ \vdots \\ y_2(t-P) \\ \vdots \\ y_N(t) \\ y_N(t-1) \\ \vdots \\ y_N(t-P) \end{bmatrix} \quad (6)$$

As can be seen, x(t) has all gene expression signals and the delayed version of these signals in it. The present invention, unlike methods utilized previously, has the ability to identify the sources s(t) that can generate such a dynamic system.

As discussed above, conventional grouping techniques (including ICA) have required that the number of clusters be pre-specified. As with other analysis techniques, choosing an unrealistic number of clusters can result in groups that are too small and unevenly scattered, or too large with unacceptably large inter-cluster variation. In addition, when an unsuitable estimation of the number of clusters is used, correlating the resulting non-optimal clusters with the physiological or biological changes can be very challenging, because many of the resulting clusters do not have truly significant biological significance.

In an embodiment, the present invention uses nonlinear ICA (NICA) for clustering of genes into independent components. In an embodiment, the methods, products and software of the present invention correlate at least one of the measured signals, x, to the underlying source(s), s, generating the signal, and experimental noise, n. Thus, in an embodiment, the methods, products and software of the present invention correlate at least one of the measured signals, x, to the underlying sources, s, generating the signal, and experimental noise, n, as a function of time, t, such that: $x(t) = f(s(t))+n(t))$, where n(t)) is additive noise, and $f(.)$ describes the nonlinear mapping (mixtures). In one embodiment, $x(t) = [x_1(t), x_2(t), \ldots x_K(t)]$ and $s(t) = [y_1(t), y_2(t), \ldots y_P(t)]$, where $x_i(t)$ represents the expression level of gene i at time t and $y_j(t)$ denotes the value of the jth component at time t.

As described herein, for NICA, a multilayer perceptron (MLP) network may be used to model the nonlinearity of the system. The equation of MLP mapping is:

$$x(t) = f(y(t)) + n(t) = B \tan h(As(t)+a)+b+n(t)$$

where the matrices A and B are the weights of the first and second layers, and vectors a and b are the corresponding bias terms.

The main goal of "learning" or "training the model" (i.e., finding the optimal values of A, B, a and b) is to approximate the posterior probability distribution function (PDF) of all the unknown values in the model, by minimizing a cost function defined based on posterior PDFs. After obtaining the optimal set of parameters A, B, a, and b, the sources can be estimated by training the neural network and applying cost minimization and back propagation methods known in the art (e.g., Hartemink et al., 2002; Lappalainen et al., 2000). The algorithm is a reversible process because after applying any change on the sources the new observation can be reconstructed by the network.

In an embodiment, the technique is applied to obtain major trends which then represent "clusters" or "state variables" (i.e., prototypes of the clusters or independent components) facilitating the estimation of the expression values for all genes. In an embodiment, the expression value of all genes in a specific number of time steps comprise the "observations" in the nonlinear components analysis, and the major trends of the genes are the "sources."

In an embodiment, the plurality of measured signals correspond to hybridization data used to measure the expression of a gene or a plurality of genes. For example, in an embodiment, the plurality of measured signals comprise a plurality of known DNA sequences hybridized to mRNA isolated from the at least one cell type. In an embodiment, the plurality of known DNA sequences are arranged to form a solid-state array. For example, microarrays such as those commercially available from Affymetrix (Santa Clara, Calif.) may be used.

Figure 2:
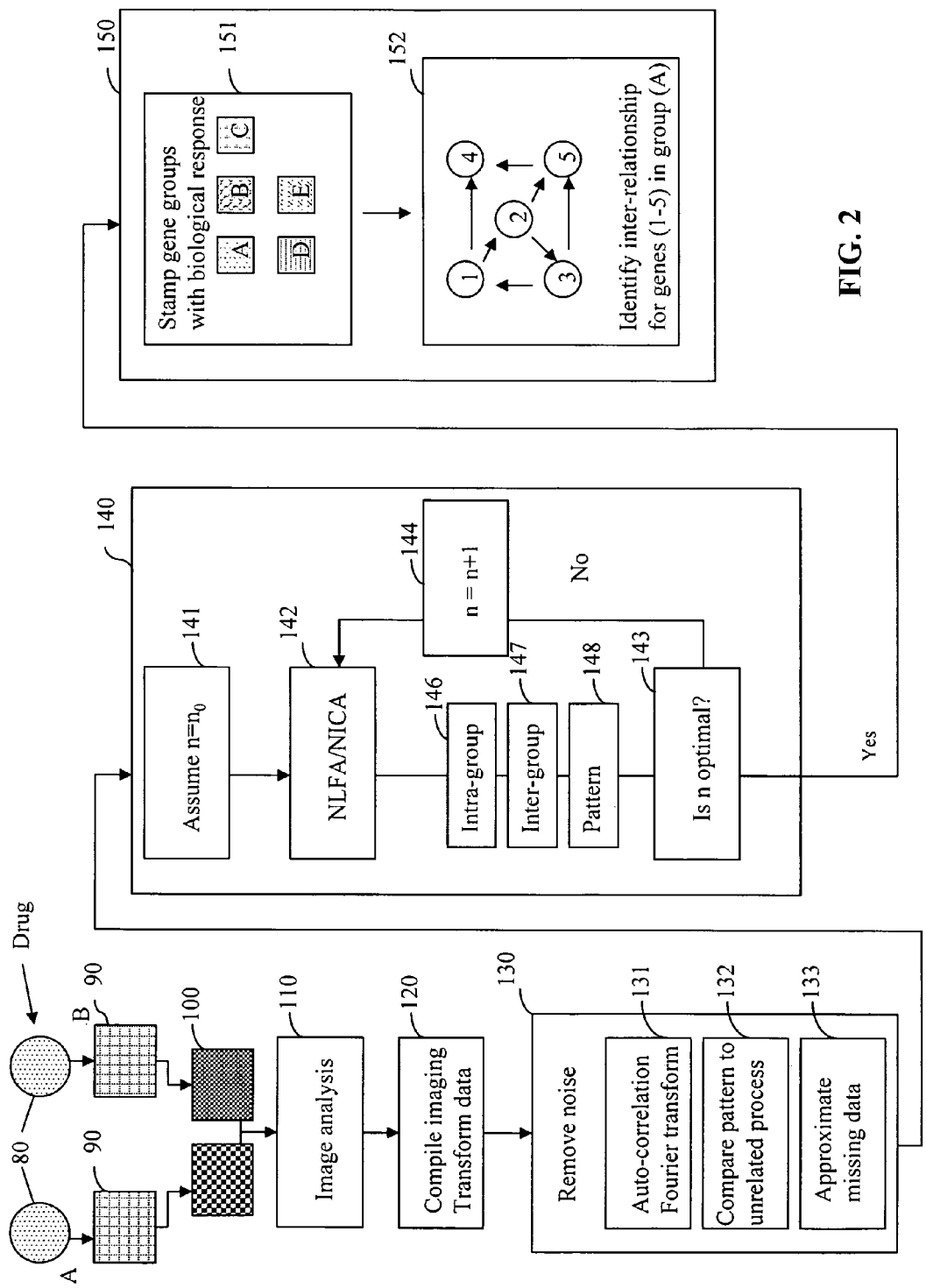
FIG. 2 shows a schematic diagram of a method for array analysis in accordance with an embodiment of the present invention in which a nonlinear independent component analysis (NICA) is used to group gene expression profiles.

A more detailed block diagram of a method of the present invention is shown in FIG. 2. First, mRNA may be isolated from an individual or a cell type of interest. For example, in an embodiment, mRNA may be harvested from cells (80) before (A) and after (B) treatment of the cells with a drug. The mRNA can then be labeled in some manner, as for example with a fluorescent tag, and hybridized to an array (or microarray) of DNA fragments (90). Generally, the array of DNA fragments comprises individual DNA fragments of known sequence at each position on the array. Thus, the DNA at one position may comprise a first sequence, the DNA at a second position may comprise a second sequence, and so on. Under the proper experimental conditions, the mRNA that has a sequence complementary to the DNA fragment at a particular address will hybridize to the DNA at that address, but not to DNA fragments at other addresses. In this way, a pattern of hybridization signals, comprising mRNA bound to the array is generated (100). As is known in the art, the hybridization pattern generated will depend on the mRNA pool being hybridized to the array, as well as the experimental conditions used for hybridization. For example, the data may comprise expression levels correlated to a biological response, such as bone healing.

In an embodiment, hybridization of the array to (A) mRNA and (B) mRNA may be done as a separate hybridizations. Alternatively, the hybridization may be performed such that mRNA (A) is labeled with a green fluorophore and mRNA (B) is labeled with a red fluorophore. In this way, hybridization for the two mRNA pools is conducted under identical conditions and imaging software may be used to quantitatively distinguish the signals.

NICA of array hybridization data may utilize either the raw data (i.e., in linear scale) or may apply the data transformed in some manner (120). For example, the analysis may employ log scaled data in form of $y_i(t) = \log_2(R_i(t)/G_i(t))$, where R and G represent two different profiles of gene expression measured using red and green fluorophores. For example, as described above, in addition to the experimental samples labeled with a red fluorophore, a control (e.g., prior to fracture) labeled with a green fluorophore is included. Thus, the multi-dimensional time-series y(t) may represent the log ratios of experimental (red) and green (reference) intensities at time, t. Also, in many cases nonlinear functions may be used to describe gene expression, as for example where expression includes multiplicative effects from enzyme cascades, lags in causality, or oscillatory behavior (e.g., Lee and Batzogou, 2003).

A variety of systems known in the art may be used for image analysis (110) and compiling the data (120). For example, where the mRNA is labeled with a fluorescent tag, an fluorescence imaging system (such as the microarray processor commercially available from AFFYMETRIX®, Santa Clara, Calif.) may be used to capture, and quantify the extent of hybridization at each address. Or, in the case where the mRNA is radioactive, the array may be exposed to X-ray film and a photographic image made. Once the data is collected, it may be compiled to quantify the extent of hybridization at each address as for example, using software to convert the measured signal to a numerical value.

In an embodiment of the present invention, the first step of signal analysis after the imaging data has been collected (110) and collated and/or transformed into a quantitative signal (120), is to filter noise from the data (130). In an embodiment, filtering may be conducted via a thresholding mechanism in which genes whose expression levels are always less than the noise level for the microarray are removed from the pool. Alternatively, variance normalization techniques may be applied to the data. Such variance normalization may include, but is not limited to, statistical techniques on based on the normalization around mean, median, start point, or the end-point. Software for performing data normalization as a means to remove noise from data sets includes, but is not limited to, MATLAB® (The MathWorks, Natick, Mass.) and SAS (SAS Institute, Inc., Cary, N.C.).

In an embodiment, an autocorrelation function and/or power spectra of the expression signals based on the Fourier Transform of the correlation function may be applied to remove noise from the data (131). In this approach, the autocorrelation of the time signal for each gene is calculated, and based on the smoothness of the autocorrelation function, as well as the power spectra, noise-like variation may be eliminated using predetermined statistical criteria. Autocorrelation is used to detect non-randomness in variables. Patterns having a spike-like autocorrelation function or a flat power spectra are most likely to be noise patterns and thus, may be filtered out.

Also, the method and systems may further comprise using an independent method to analyze the identified independent components for biological relevance. For example, the data may be compared to the known biological changes of interest to determine if outlying signals may be due to obvious experimental or human error, or created by another biological process that is not of interest in the conducted experiments (132). This allows the user to intelligently eliminate or reduce the chances of corrupting the results with noisy or non-relevant data. As an example, the gene variations due to stress are known to corrupt gene expression data in many experiments. If the pattern of gene expression associated with such environmental factors is known (e.g., the pattern of gene expression associated with heat-shock or other types of stress), the genes highly correlated with this factor can be identified and removed from the pool of genes to be investigated for other types (i.e., non-stress related) of biological interactions.

Finally, there may be an analysis whereby missing data is approximated (133). For this, in time-series, spline approximators may be used to estimate the missing data points if the neighboring points in the time series are known (Ziv Bar-Joseph, et al., Proc. Natl. Acad. Sci., U.S.A., 100:10146-10151, 2003).

Still referring to FIG. 2, once the signals have been corrected for noise, they may be passed to the next step: nonlinear independent component analysis (NICA) or nonlinear factor analysis (NLFA) for the determination of the number of gene groups (140). For iterative NICA or iterative NLFA, a small number $n=n_0$ (in many cases $n_0=2$) is chosen as the initial guess for the number of independent gene expression groups (141). With the assumption $n=n_0$ a NICA or NLFA algorithm is performed on the data (142) and the fit of the data to the model is evaluated (143). The data then analyzed for an increasing number of independent groups until the fit of the data no longer improves (144). Thus, for NICA (and NLFA), the back propagation algorithm used to solve for A, B, a, and b, is an iterative algorithm that sequentially updates the values of A, B, a and b as is known in the art. The number of independent gene groups providing the best fit is then chosen as the optimal number of independent components.

Thus, embodiments of the present invention comprise the use of iterative nonlinear component analysis (e.g., iterative NICA or iterative NLFA) to generate clusters that are independent and meaningful. Assuming that $n=n_0$ is a reasonable assumption (i.e., that the user has pre-selected the correct number of gene groups), the analysis is complete. In most cases, however, an analysis based on a pre-determined number (or initial estimate $n_0$) of gene groups is often far from reality and must be improved. For example, the assumptions made on the number of clusters are often based on the underlying biological factors, and may or may not be accurate. For biological studies where the number of gene groups can be guessed, $n_0$ is usually selected to be an integer slightly smaller than the estimated number. For the applications where biology cannot provide an estimation of the underlying gene groups, $n_0$ is set to number 2. Regardless of the suitability of the initial value of $n=n_0$, the algorithm of the present invention will search for the optimal number of the gene groups.

To optimize the number of clusters, the fit of the data with an increasing number of clusters may be quantitatively assessed. The number of clusters is sequentially increased (i.e., from $n_0$, to $n_0+1$, to $n_0+2$, ... to $n_0+i$) until the fit starts to decrease. At this point, the previous number of clusters is selected as optimal (e.g., $n_0+(i-1)$).

At least four criteria may be used for cluster optimization: (1) maximizing the mutual information (i.e., correlation) within each of the resulting groups (146) (compared to the previous values of n); (2) minimizing the mutual information between (outside of) groups (147) (compared to the previous values of n); (3) minimizing the information distance (i.e., hyper-volume) within each of the resulting groups (146) (compared to the previous values of n); and (4) maximizing the information distance (i.e., hyper-volume) between each of the resulting groups (147) (compared to the previous values of n). Additionally, in yet a further embodiment, the groups are evaluated to be sure that each group has a unique pattern (i.e., no two groups describe the same expression profile) (148).

Thus, for the first iteration when $n=n_0$, it is always assumed that the condition is non-optimal and therefore, the new value of n is set as $n=n+1$. In subsequent iterations, the criteria described above are tested and if the condition is not yet optimal, n is incremented. At some point, however, it is determined that a condition is in fact optimal (i.e., a minimal intra-group variance and maximal inter-group variance), such that any further increase in the number of clusters reduces the fit. At this point, clusters obtained with the previous value of n are chosen to be optimal and are sent to the next step. In an embodiment, the number of clusters defined accurately approximates the number of gene groups, or independent biological processes(s).

For linear ICA, the results of the dynamic ICA algorithm yield three matrices. The first matrix defined by ICA contains a set of basis functions (i.e., s(t) in formulas above). The second matrix contains the mixing matrix (i.e., A in the formulas above), and the third matrix contains the separating matrix (W). For MPS nonlinear techniques, the algorithm also yields three matrices: the sources are on the top layer; observations are on the bottom layer; and the middle layer consists of hidden neurons each of which computes a nonlinear function of the weighted summation of the inputs.

There are many types of algorithms that may be used for the analysis techniques of the present invention. For example, nonlinear ICA algorithms (such as P. Pajunen, A. Hyvärinen and J. Karhunen "Non-Linear Blind Source Separation by Self-Organizing Maps" *Proc. Int. Conf. on Neural Information Processing*, Hong Kong, pp. 1207-1210, 1996; Yang, H. H., et al., "Information-theoretic approach to blind separation of sources in non-linear mixture", Signal Processing archive, Volume 64, Issue 3, February 1998; —M. Solazzi and A. Uncini, "Spline neural networks for blind separation of post-nonlinear-linear mixtures", IEEE Transactions on Circuits and Systems I: Fundamental Theory and Applications, Volume: 51:817-829, 2004.) may also be employed.

There are, however, certain disadvantages associated with existing nonlinear techniques. For example, ICA is computationally intensive when applied to a large number of inputs assuming different number of independent components. Thus, if ICA is to be performed iteratively, the recursive process on a large set of inputs can be computationally time-consuming. In addition, traditional ICA algorithms do not provide information about the dynamics and time convolutions of the signals. Thus, traditional ICA methods are "static" nature, in that the information provided for one point in time is not correlated to information at other points in time.

In an embodiment, the algorithm has a hierarchical structure that reduces the computational complexity of the algorithm. For example, when performing hierarchical ICA, after a new independent component is generated, the inputs that have been estimated by the linear/nonlinear combination of the existing independent components (based on the mixing matrix) may be removed from the pool of inputs. In this way, at each step, some of the signals (i.e., genes) are removed from the pool and ICA is performed on a smaller number of remaining genes in the next step. Thus, the number of inputs after the generation of the first few components is significantly reduced, thereby making the iterative process much faster. Hierarchical methods reduce the computational complexity of the calculations exponentially as the analysis proceeds. Also, hierarchical methods provide a more accurate clustering technique in that the threshold values for each cluster may be adaptively tuned throughout the analysis. This adaptive tuning can avoid generation of overly large clusters with poorly correlated samples. Such tuning has been shown to reduce the generation of overly small and condensed clusters.

Also, in an embodiment, a type of dynamic ICA is used for the analysis. Attributes of dynamic ICA algorithms which make these algorithms particularly suited for array analysis include improved matrix utilization and the inclusion of the dynamics of variations of the measured effect over time. An application of such a method would be quantitative dynamic modeling and analysis of the effect of a drug on genetic pathways involved in a disease throughout the course of treatment. Standard (non-dynamic) ICA algorithms provide for the separation of signals but do not adjust the analysis to explain with the effect of the convolution of signals in time.

Once the genes have been clustered into separate groups, the next task is to determine what genes are included in the group. Hybridization based assays are designed to measure the relative levels of signal present at each address. Thus, in some cases, there may be a background signal even for genes that are not being expressed by the cell type being assayed. Because of the high levels of background or other types of noise prevalent in these types of experiments, in many cases, a linear combination of the original input does not yield a simple zero contribution for genes not used on the pathway. Thus, in an embodiment, a decision must be made about what cutoff is useful for choosing a gene's contribution to the pathway.

B. Correlation of Gene Groups and Defining the Interrelationships Between Genes in a Group In the next step, gene groups identified by the method used for clustering may be matched to particular biological response pathway (150) (FIG. 2). For example, as described above, it may be determined that genes in group 1 display a profile similar to known metabolic genes, whereas genes in group 2 are involved in cholesterol metabolism, genes in group 3 are involved in carcinogenesis, and genes in group 4 are involved in bone healing. Additionally or alternatively, the relationship among genes within a group may be defined (152) (FIG. 2).

1. Correlation of Group to Biological Response

To correlate a specific gene cluster to a biological pathway or response, the pattern of gene expression for each group may be compared to a signal that shows the observed biological events or changes. For example, the biological event(s) may be the amount of cartilage formation during the healing of bone.

Thus, the first step involves determining whether any of the clusters identified by nonlinear grouping of gene expression data are correlated with, and therefore may be biologically relevant to, a particular physiological process. If signals representing the biological/physiological changes are available, the correlation among the measured signal(s) for each cluster as determined by nonlinear component analysis can identify the clusters that are correlated with the biological or physiological response under study. In this way, a particular independent component, or gene group, is identified (or "stamped") as being involved in the physiological process or biochemical pathway of interest.

For example, it may be found that out of 10 independent components (e.g., gene groups 1-10) group 3 has patterns of gene expression that are correlated to the process of bone re-growth. Genes in group 3 would then be "stamped" as being involved the bone healing.

2. Modeling the Interaction Between Genes within a Group

In an embodiment, once the clusters involved in a biological study are identified, the genes of the relevant clusters are placed into set for further analysis. This pool of genes may comprise a set of "potential members" of the pathway for the biological changes of interest. Next, dynamic mathematical modeling is applied to relate the expression levels of each of the prototypes in all gene clusters to each other. The model relates the future expression level of the prototypes of gene clusters ($y_i$'s) to the values of other prototypes in the past time(s). For example, the genes in a cluster may comprise a pool of candidate genes that may be involved in mediation of a biological change of interest. For example, the biological change of interest may comprise bone re-growth and there may be five genes in the cluster identified as important for bone re-growth.

In an embodiment, the methods and systems of the present invention comprise the use of dynamic mathematical modeling to relate the expression levels of each of the genes in the cluster pool to each other. The model may be linear or nonlinear. In an embodiment, the modeling comprises autoregressive (AR) or autoregressive exogenous (ARX) modeling.

Or, the modeling may comprise moving average modeling. In yet another embodiment, the modeling may comprise a Box-Jenkins Approach.

Preferably, the model relates the expression level of all genes ($y_1, y_2, y_3, \ldots y_N$) to each other and to the environmental (e.g., physiological) factors ($u_1, u_2, u_3, \ldots u_M$), such as concentration of a chemical, temperature, or other type of treatment. The model may also estimate the level of uncertainty inherent to the model by considering a noise factor (e) in the equations. Thus, the model may be shown as follows:

$$y_i = f(y_1, y_2, \ldots, y_N, u_1, \ldots u_m) + e \tag{7}$$

It can be seen that in its most general form, the model is a nonlinear. In many cases, however, a linear model provides a good fit to the data. This might be expected in the situation where the genes of interest act relatively independently. An example of a linear model is as follows:

$$y_i = a_{i1}y_1 + a^{i2}y_{i2} + \ldots + a_{iN}y_N + a_{ie1}u_1 + \ldots + a_{ieM}u_M + e \tag{8}$$

where: $y_i$ is the expression of the gene i, $u_j$'s represents the environmental factors involved in the biological process under study, and e is the noise factor. The model may or may not include time (t) as a factor. If the time factor is added, then the equation may consider the expression levels of all genes as well as the presence of environmental factors in a few past time samples. An example of a model describing environmental factors, time factors, and noise is as follows:

$$y_i(t) = f(y_1(t-1), y_1(t-2), \ldots y_1(t-n_{a1}), y_2(t)y_2(t-1), \ldots,$$
$$y_2(t-n_{a2}), \ldots, y_N(t), y_N(t-1), \ldots,$$
$$y_N(t-n_{aN}), u_1(t), U_1(t-1), \ldots, U_1(t-n_{b1}), \ldots,$$
$$u_M(t), u_M(t-1), \ldots, U_M(t-n_{bM})) + e(t) \tag{9}$$

where: $n_{ai}$ and $n_{bj}$ are the degrees with respect to gene i and environmental factor j. In case of a linear model, the equation is reduced to:

$$y_i(t) = -a_{i11}y_1(t-1) - a_{i12}y_1(t-2) - \ldots - a_{i1n_{a1}}y_1(t-n_{a1}) - \tag{10}$$
$$a_{i20}y_2(t) - a_{i21}y_2(t-1) - \ldots - a_{i2n_{a2}}y_2(t-n_{a2}), \ldots, +bu_1(t),$$
$$u_1(t-1), \ldots, u_1(t-n_b), \ldots, u_M(t), u_M(t-1),$$
$$\ldots, u_M(t-n_{bM})) + e(t)$$

This type of analysis is an adaptation of the analysis used for linear Auto-Regressive exogenous (ARX) modeling. As described above, in some cases, variations of gene expression over time may be incorporated into the analysis. Thus, in an embodiment, the present invention comprises ARX modeling to relate genes in different consecutive time steps throughout the experiment.

For simplicity, a one-dimensional case is described. In the one dimensional case, the equations describe the situation where one gene is dynamically interacting with the environment. In an embodiment, extension of the equations to multi-dimensional case, where a number of genes are involved, may be performed. For the one dimensional case, the relation between the expression level of a gene at time t, y(t) is as:

$$y(t) + a_1 y(t-1) + \ldots + a_{n_a} y(t-n_a) = b_i u(t-1) + \ldots + b_{n_b} u(t-n_b) + e(t) \tag{11}$$

where y is gene expression (output), u is the environmental factor related to the biology study (i.e., exogenous input such as drug concentration), and e is the effect of other interfering environmental factors and experimental noise. The main objective is to determine the coefficients $a_1, a_2 \ldots$ and $a_{n_a}$ though which the model is completely defined. Defining θ as the vector of parameters as shown below:

$$f = (a_1 a_2 \ldots a_{n_a} b_1, b_2, \ldots, b_{n_b}) \tag{12}$$

to predict the coefficients of equation (11), $\epsilon(t, \theta)$ may be defined as the prediction error as follows:

$$\epsilon(t, \theta) = y(t) - \hat{y}(t|\theta) \tag{13}$$

where $\hat{y}(t|\theta)$ is the predicted output given the set of parameters θ. Next, the prediction-error sequence may be processed through a stable linear filter L(q):

$$\epsilon_F(t, \theta) = L(q)\epsilon(t, \theta) \tag{14}$$

where q stands for an element of delay. Then, using $V_N(\theta, Z^N)$ as defined below, the total error (averaged over all data points) may be measured:

$$V_N(\theta, Z^N) = \frac{1}{N} \sum_{t=1}^{N} l(\epsilon_F(t, \theta)) \tag{15}$$

where l(.) is any scalar-valued (positive) measure function (often defined as the square function). The parameter estimation is then defined as finding a set of parameters that minimizes the total error function (16).

$$\hat{\theta}_N = \hat{\theta}_N(Z^n) = \arg\min_{\theta \in D_M} V_N(\theta, Z^N) \tag{16}$$

To obtain these parameters, the least-squares method is applied. It may be assumed that $$\hat{y}(t|\theta) = \phi^T(t)\theta \tag{17}$$

where φ is the regression vector defined as shown by equation (18).

$$\phi(t) = [-y(t-1) - y(t-2) \ldots -y(t-n_a) u(t-1) \ldots u(t-n_b)]^T \tag{18}$$

With equation (18) the prediction error is defined by equation (19).

$$\epsilon(t, \theta) = y(t) - \phi^T(t)\theta \tag{19}$$

With L(q)=1 (i.e., identify filter), and $$l(\varepsilon) = \frac{1}{2}\varepsilon^2$$

(i.e. the square function), the total averaged error criterion function is defined by equation (20).

$$V_N(\theta, Z^N) = \frac{1}{N} \sum_{t=1}^{N} \frac{1}{2} [y(t) - \varphi^T(t)\theta]^2 \tag{20}$$

Equation (20) is the least-squares (LS) criterion for the linear regression and it can be minimized analytically to gives the equation (21) as the solution.

$$\theta_N^{LS} = \arg\min \hat{V}_N(\theta, Z^N) = \left[\frac{1}{N} \sum_{t=1}^{N} \varphi(t) \partial^T(t)\right]^{-1} \frac{1}{N} \sum_{t=1}^{N} \varphi(t) y(t) \tag{21}$$

Having calculated the set of parameters, the ARX model is completely defined and can be used for microarray time-series processing application. Although the ARX model can be derived for individual genes, the present invention recognizes that when the number of genes is very large, the ARX model can be created based on the independent components determined by nonlinear component analysis, i.e., instead of using individual gene expression as y(t)'s, independent components can be used y(t)'s in the ARX model.

Once a model describing the interrelationship between genes $y_1, y_2 \ldots y_n$, has been generated, it may be "pruned" to eliminate the weak links. In the pruning step, links that are statistically insignificant may be removed from the pathway. For example, for the linear case, the links ($a_{ij}$) may be tested for significance and links that are not significantly large may be removed. Such a process may be done in an iterative manner, in which the effect of removing a selected link or links is evaluated in terms of statistical fit. For example, if all the links originating or ending at a particular gene or environmental factor are set to zero, the gene or environmental factor is completely removed from the pathway.

Figure 3:
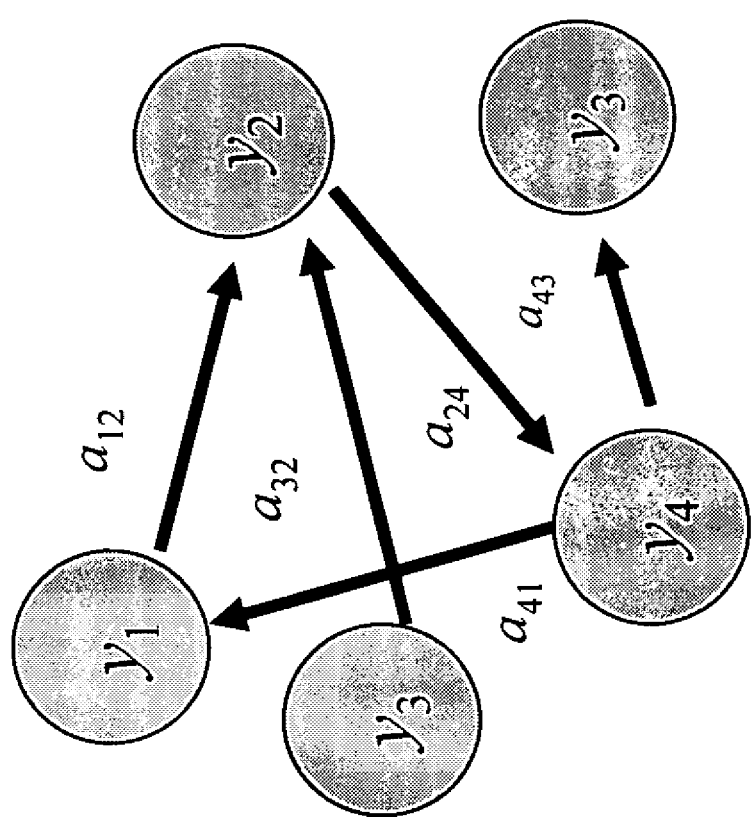
FIG. 3 shows a schematic depicting the interrelationship of four genes out of a larger network of genes as defined using autoregressive exogenous (ARX) modeling in combination with linear ICA to cluster the genes.
Figure 4A:
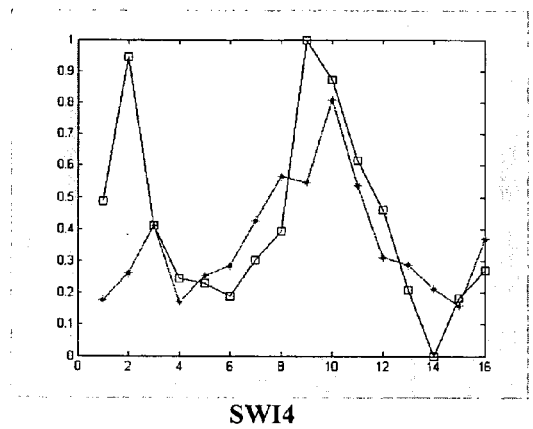
FIG. 4 shows predicted and actual expression patterns for known genes expressed in various phases of the yeast cell cycle as defined using autoregressive (AR) modeling in combination with linear ICA. Expression profiles for genes at various points of the yeast cell cycle are as follows: Early G1 phase: Panel 4A—SWI4; Panel 4B—CDC46; Early G2 phase: Panel 4C—SWE1; Panel 4D—GIN4; S phase: Panel 4E—NUD1; Panel 4F—CIN8; G2 phase: Panel 4G—CSE4; Panel 4H—ELM1; and M phase: Panel 4I—CDC20; and Panel 4J—DBF2. In each graph, the x axis is the time of cell growth in hours and the y-axis is the level of gene expression measured using a hybridization based assay. The actual genes assayed are listed below each graph.
Figure 4B:
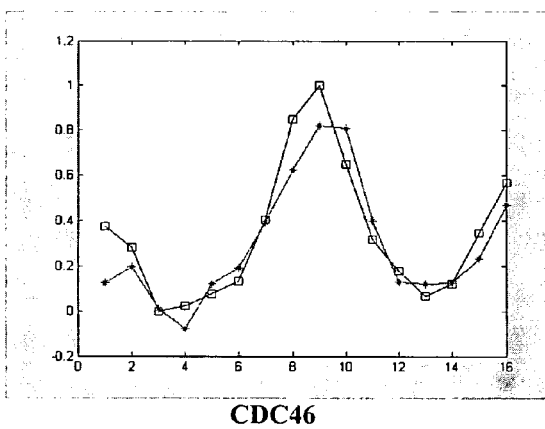
Figure 4C:
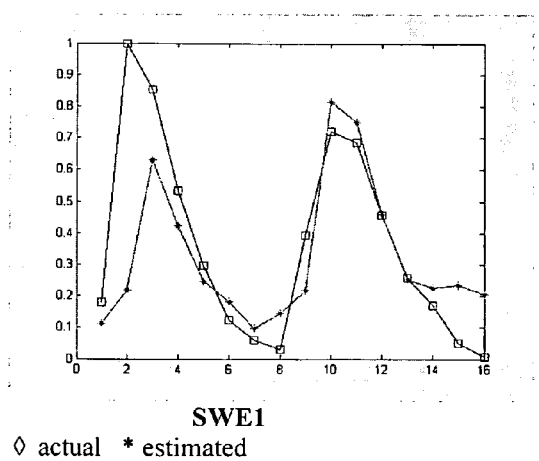
Figure 4D:
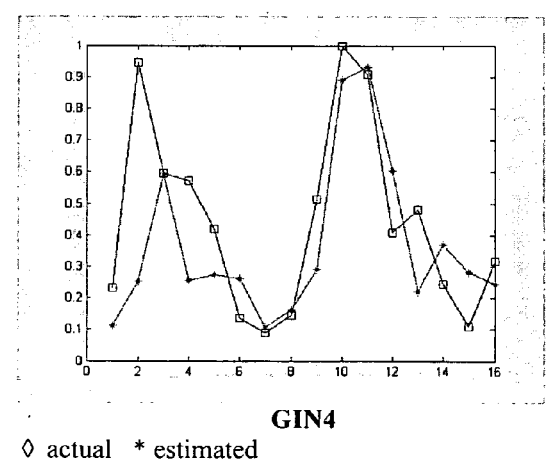
Figure 4E:
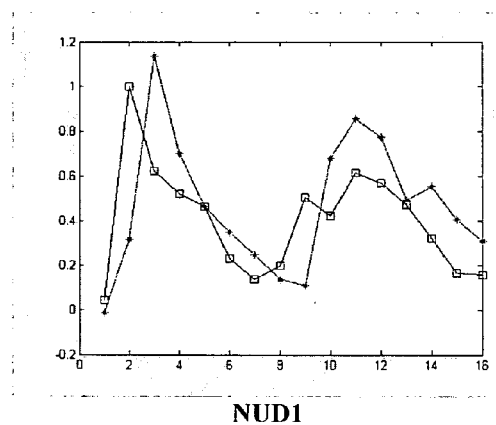
Figure 4F:
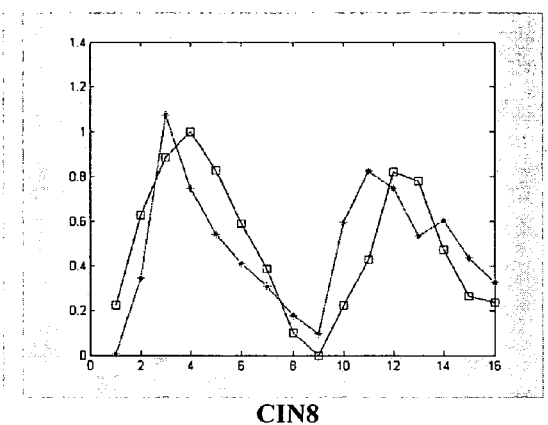
Figure 4G:
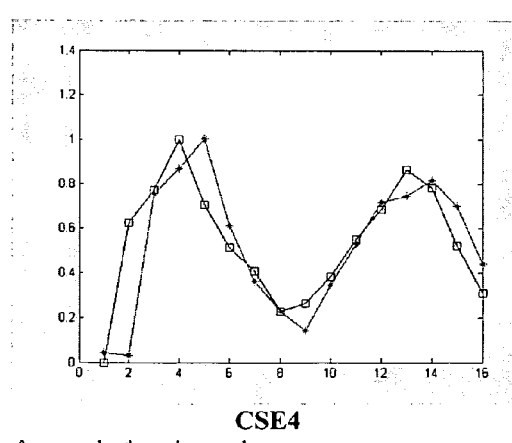
Figure 4H:
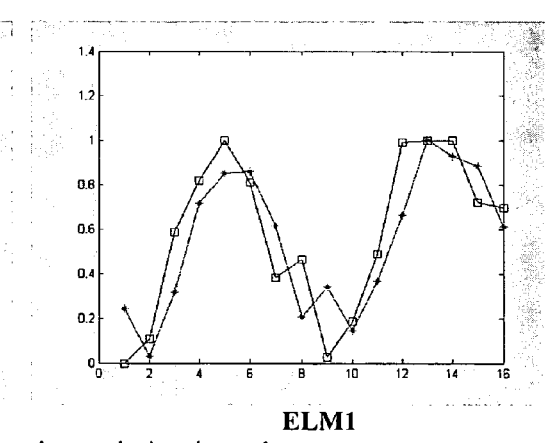
Figure 5A:
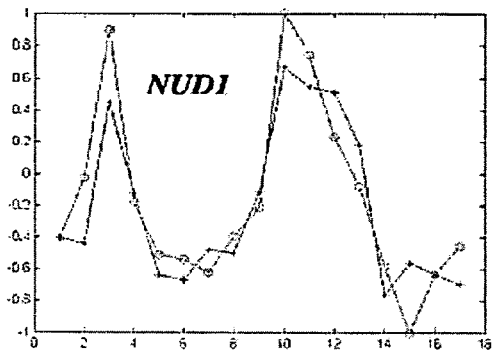
FIG. 5 shows predicted and actual expression patterns for known genes expressed in various phases of the yeast cell cycle in accordance with an embodiment of the present invention in which nonlinear independent component analysis (NICA) is used in conjunction with autoregressive exogenous (ARX) modeling to group gene expression profiles, and an inverse analysis with NICA is used to predict the behavior of individual genes. The following genes were analyzed: Panel 5A—NUD1; Panel 5B—BUD2; Panel 5C—CIK1; Panel 5D—HUS2; Panel 5E—NUF1; Panel 5F—CIN8; Panel 5G—CDC6; Panel 5H—ACC1; Panel 5I—STU2. In each graph, the x axis is the time of cell growth in hours and the y-axis is the level of gene expression measured using a hybridization based assay. The actual genes assayed are listed below each graph.
Figure 5B:
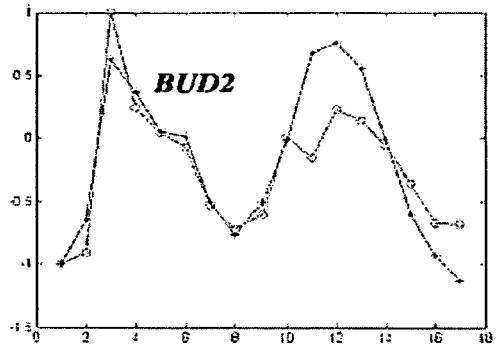
Figure 5C:
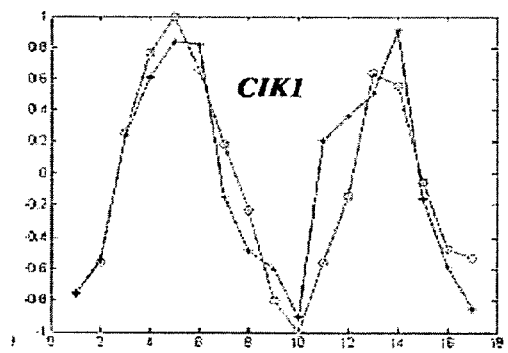
Figure 5D:
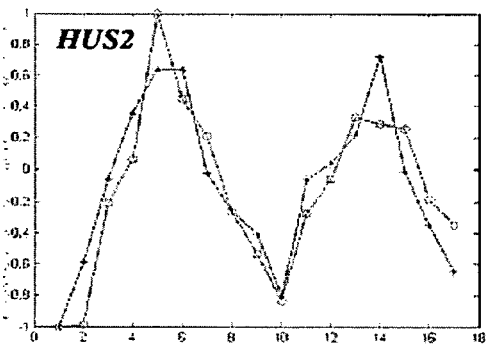
Figure 5E:
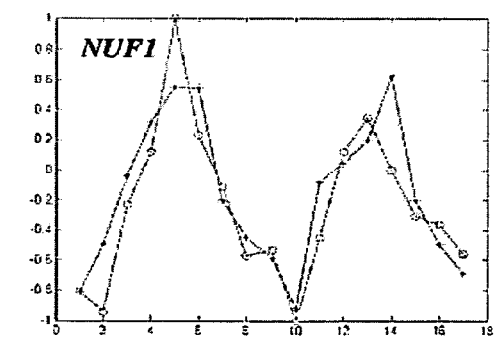
Figure 5F:
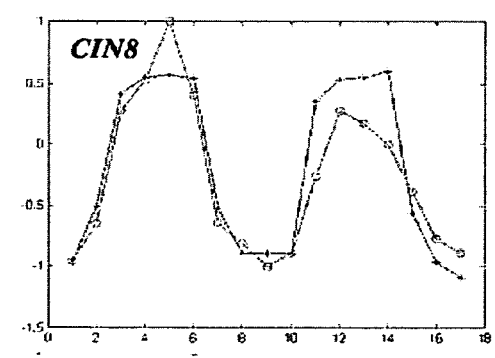
Figure 5G:
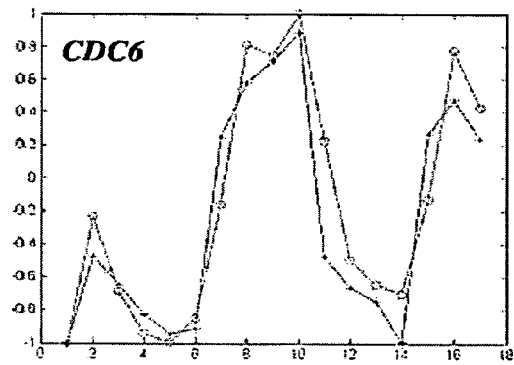
Figure 5H:
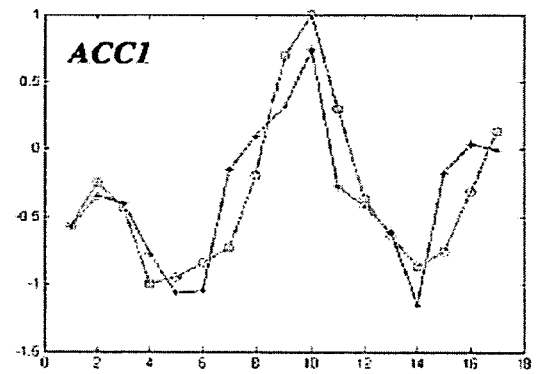
Figure 5I:
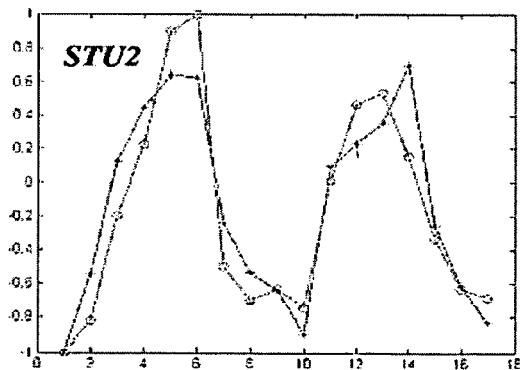

After this pruning process, a simplified version of the pathway may be generated. In an embodiment, the simplified model may be visualized and understood as a graphical representation of the pathway. An example of a pathway after pruning, and assuming only genes (i.e., $y_1, y_2, y_3$, and $y_4$) and not environmental factors (e) is shown in FIG. 3. For example, in the model shown in FIG. 3, vectors $a_{21}$, $a_{23}$, and $a_{14}$ have been removed.

At the pruning state, the significance of the surviving links may be evaluated or "ranked" using a standard statistical test of fit such as T-test. In this analysis, links that play more important roles are ranked higher. In a visual representation, the stronger links with higher significance may be shown with thicker arrows.

In an embodiment, modifications of the formulation are used to provide a multi-variable model. In the p dimensional case of equation (1), where the expression levels of p genes at previous and present times are related to each other, θ and φ(t) are generalized as:

$$\theta = (A_1 A_2 \ldots A_n) \quad (22)$$

and $$\phi(t) = [-Y(t-1) - Y(t-2) \ldots -Y(t-n)]^T \quad (23)$$

where $$A_k = \begin{pmatrix} a_{k11} & a_{k12} & \cdots & a_{k1p} \\ a_{k21} & a_{k22} & & a_{k2p} \\ & & & \\ a_{kp1} & a_{kp2} & & a_{kpp} \end{pmatrix} \quad (24)$$

and $$Y(t) = [y_1(t) \ldots y_p(t)]^T \quad (25)$$

The function l(ε) is modified as:

$$l(\varepsilon) = \frac{1}{2} \varepsilon^T \Lambda^{-1} \varepsilon \quad (26)$$

where Λ is a symmetric positive semi definite p×p matrix that weighs the relative importance of the components of ε. Also, for multi-variable case, $$V_N(\theta, Z^N) = h(Q_N(\theta, Z^N)) \quad (27)$$

where $$h(Q) = \frac{1}{2} tr(Q \Lambda^{-1}) \quad (28)$$

and, $$Q_N(\theta, Z^N) = \frac{1}{N} \sum_{t=1}^{N} \varepsilon(t, \theta) \varepsilon^T(t, \theta) \quad (29)$$

For a p dimensional case, the LS criterion takes the form shown as equation (30).

$$V_N(\theta, Z^N) = \frac{1}{N} \sum_{t=1}^{N} \frac{1}{2} [y(t) - \varphi^T(t)\theta]^T \Lambda^{-1} [y(t) - \varphi^T(t)\theta] \quad (30)$$

This leads to the following equation (31) to find the model parameters in multidimensional cases.

$$\hat{\theta}_N^{LS} = \left[ \frac{1}{N} \sum_{t=1}^{N} \varphi(t) \Lambda^{-1} \varphi^T(t) \right]^{-1} \frac{1}{N} \sum_{t=1}^{N} \varphi(t) \Lambda^{-1} y(t) \quad (31)$$

Application of the methods and systems of the present invention to the analysis of gene expression data can identify genes that are correlated in both the same sense as well as in the opposite sense for the same biological process of interest. Genes that are correlated in the same sense are genes whose relative levels of expression react in the same manner to a given stimulus. Genes that are correlated in the opposite sense are genes whose relative levels of expression react in an opposite manner to a given stimulus. For example, the stimulus of a change in temperature may be associated with an increase in expression for genes A and B and an inhibition of expression for gene C. In this case, genes A and B are correlated in the same sense with each other, but in an opposite sense with gene C. For example, whereas some genes have almost identical profiles (at least qualitatively), other gene profiles are almost mirror images to each other.

Also, the methods and systems of the present invention can also identify genes that have a delayed response as compared to other genes in the group. For example, in some cases, gene E is activated in response to activation of gene D. Thus, activation of gene E may be delayed relative to gene D. Signals for genes that have a delayed response to other genes may appear to be shifted as compared to the triggering gene (e.g., gene D) when gene expression is analyzed as a function of time.

For example, in an embodiment, microarray gene expression data for the budding yeast *S. Cerevisiae* may be analyzed to identify the gene expression pattern during the cell cycle of the budding yeast *S. Cerevisiae*. Yeast cells may be arrested in the late G1 stage of the cell cycle by raising the temperature to 37° C., and the cell cycle reinitiated by shifting cells to 25° C., thereby obtaining a synchronous cell culture. Cells may be harvested over the course of multiple cell cycles. Genes which have been activated in each phase of cell cycle have been previously identified (Cho et al., *Molecular Cell*, 2:65-73, 1998). Thus, it is known that many S. Cerevisiae genes can be divided into five groups, according to the stage in which the gene is expressed. The first cluster includes genes primarily active in early G1, the second cluster includes genes which are active in late G1, and the third, the fourth and fifth clusters correspond to the genes which are activated in S, G2 and M phases of the cell cycle, respectively.

The main purpose of applying AR or ARX models to the data is to discover the effect that each gene has on itself and other genes in the next time steps. For this reason, gene expression (at later times) may be considered to be the output and gene expression at earlier times may be the source. For example, in the study of gene expression in yeast assayed at various points in the cell cycle, there will be multiple outputs (independent components) and no exogenous inputs (since there is no perturbation). This means that there are five outputs (one for each cell cycle phase), and u(t) may be set to zero for all time points.

The model parameters (i.e., coefficients) may be estimated using data grouped by a linear independent component analysis as the training set. To determine how well the resulting model relates the expression level of each individual gene to the other genes, the developed model may be used to predict the expression level of genes from each cluster. The predicted and true values of the expression levels for these genes are compared in FIG. 4, panels 6A-6J show the results for ten separate genes, two genes from each stage of the cell cycle. As can be seen, the model can accurately predict the expression levels.

Figure 7:
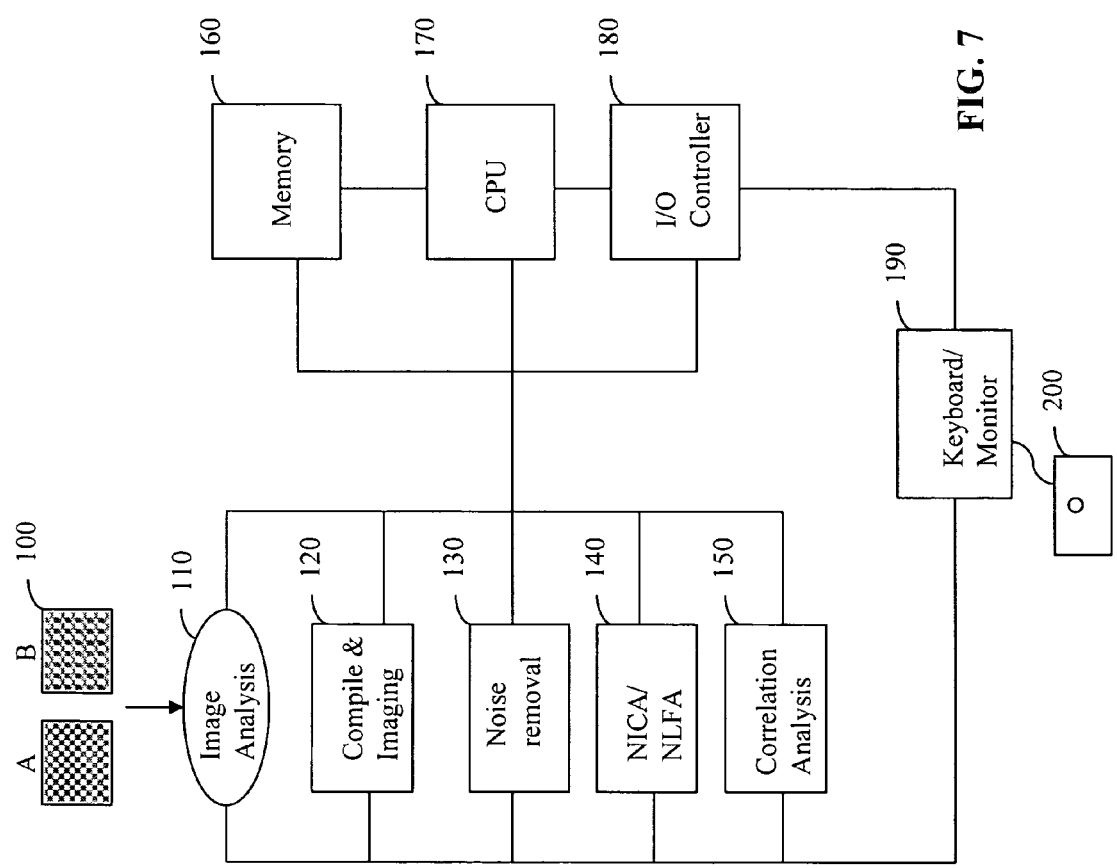
FIG. 7 shows a schematic diagram of a system for array analysis in accordance with an embodiment of the present invention.

In embodiments of the present invention, the model parameters (i.e., coefficients) may be estimated using data grouped by nonlinear factor analysis or nonlinear ICA to derive the training set. FIG. 7 shows the results for the mapping of microarray gene expression data for 40 genes from budding yeast *S. Cerevisiae* where the genes were grouped using NICA methods. In order to train the model, the first ten time points of each component were used as training data to find the NICA groups and an AR models. Then, the expression values of each component, and as a result all individual genes, were predicted for all time steps. Since the number of time points in the training data was small (i.e. eight steps in each cycle), in order to minimize the number of parameters, the degree of the model was set to one.

In an embodiment, training of an AR model is equivalent to the estimation of $a_{ij}$ coefficients, where i=1, . . . , 5, and j=1, . . . , 5. Since the degree of the model is set to 1 for all genes, the third index of the parameters is dropped. After training with the first ten time points the following values for $a_{ij}$ coefficients re obtained as:

$$A = \begin{bmatrix} -1.045 & -0.970 & 0.634 & -36.803 & -19.920 \\ 0.848 & 0.033 & -0.606 & 28.340 & 40.800 \\ 0.0860 & 0.919 & -0.780 & 26.539 & 20.936 \\ -0.0022 & 0.0004 & 0.0135 & -0.480 & -0.285 \\ 0.0065 & 0.0124 & -0.0233 & 0.433 & 0.474 \end{bmatrix}$$

Using each row of this matrix one can predict the value of one component in the next time step based on the values of the all components in the previous times. For example, for the first component, the model can be written as:

$$y_1(t) = -1.045 y_1(t-1) - 0.970 y_2(t-1) + 0.634 y_3(t-1) - 36.803 y_4(t-1) - 19.920 y_5(t-1) \quad (32)$$

Similar equations can be obtained form the matrix given above for other components. As mentioned above, the first 10 points of the data was used to train the model, and the capabilities of the model in predicting the correct values of expression in future samples are tested against all the time steps, which includes 17 time samples. To test and validate the performance of the model in estimating the future values of individual gene, the NICA (i.e., NLFA) method may be applied to all genes and after producing the major components of genes, the network of NICA (i.e., NLFA) is used to predict the expression value of each single gene in other (e.g., past or future) time steps.

In an embodiment, the model can successfully predict the trend of the expression profile for individual genes based on the expression values of all genes at the previous times. For example, the prediction results for some of the genes used in the analysis above are shown in FIG. 5 (Panels A-I), where it can be seen that for each of the nine genes, the predicted values match well with the true expression values of genes.

Figure 6:
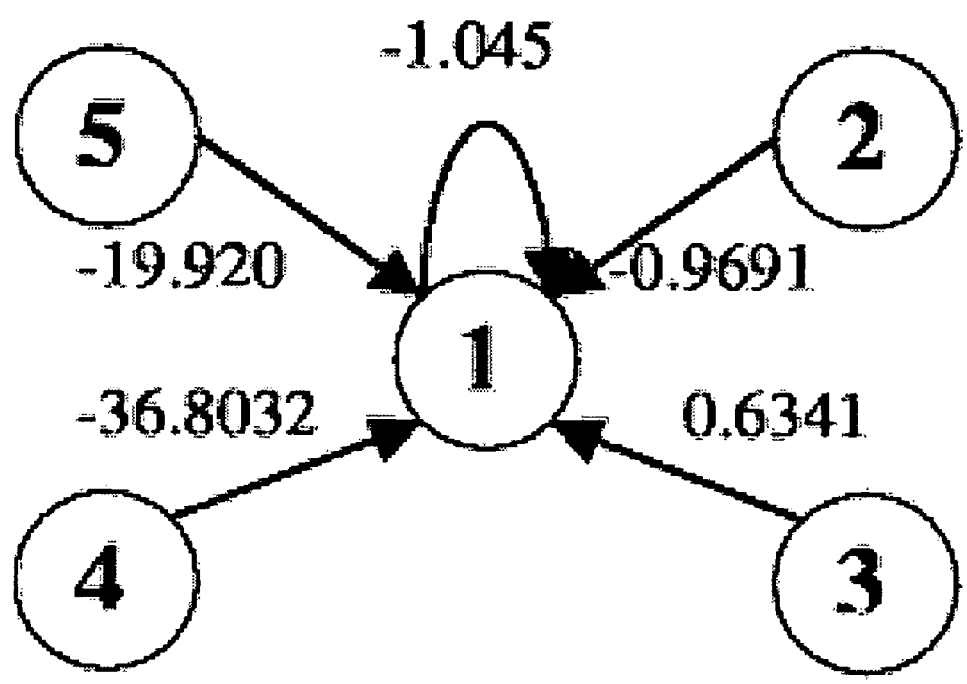
FIG. 6 shows the effect of all components on component 1 using an analysis in which nonlinear independent component analysis (NICA) is used in conjunction with autoregressive exogenous (ARX) modeling to group gene expression profiles, and an inverse analysis with NICA is used to predict the behavior of individual genes in each group in accordance with an embodiment of the present invention.

The analysis performed using nonlinear grouping and autoregressive modeling may be analyzed to describe the relationship of the gene pools between selected components to thereby represent the dynamic pathway of cell cycle processes. FIG. 6 shows such an analysis for the data used to generate FIG. 5. Such a network will show the effect of each prototype on itself and on other genes in the next time step. Since showing all 25 links and arrows would complicate the graph, in FIG. 6, only the effect of all components on the first component is depicted.

Systems for Analysis of Arrays

In an embodiment, the present invention provides systems for carrying out array analysis. Also, in an embodiment, the present invention comprises a computer-readable medium on which is encoded programming code for analyzing gene expression from a plurality of data points comprising using a nonlinear analysis to cluster the data into independent groups. In an embodiment, the nonlinear component analysis is a nonlinear factor analysis (NLFA). In an embodiment, the nonlinear component analysis is nonlinear independent component analysis (nonlinear ICA).

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, VISUAL C#®, VISUAL BASIC®, VISUAL FOXPRO®, Java, and JavaScript.

As described above, the system may comprise an imaging unit as well as a means for the user to interact with the system as the analysis proceeds. Thus, in an embodiment, the present invention further comprises a unit for collecting and/or compiling data from said plurality of measured signals and transmitting said data to said computer, and a unit for transmitting the results of said analysis to a user.

The systems of the present invention are designed for high-throughput analysis of DNA hybridization data. Thus, in an embodiment, the plurality of measured signals comprise a plurality of known DNA sequences hybridized to mRNA isolated from at least one cell type.

Also described above, in an embodiment, the system utilizes a nonlinear independent component analysis (NICA) or nonlinear factor analysis (NLFA) to provide an optimal number of independent gene groups that explain the gene expression profiles being measured. In an embodiment, the NICA or NLFA is iterative in nature. In an embodiment, the number of gene groups, n, is estimated as a preset number, $n_0$. The data may then be evaluated by increasing the number of groups from $n_0$ and performing an iterative analysis of the relative fit of the data using $n_0$ as compared to the new value of n. In an embodiment, the number of groups are increased incrementally by 1 group for each evaluation, such that the number of groups increases at each step from $n_0$, to $n_0+1$, to $n_0+2$, until the optimum number of groups ($n_{opt}$) is determined. Thus, in an embodiment, the estimation of A, B, a, and b, may be performed in an iterative manner. Also, in an embodiment, the system comprises a hierarchical nonlinear component analysis such that the complexity of the computational analysis is reduced as the analysis proceeds, by removing inputs that have been described at earlier stages of the analysis from the set of data points still remaining to be characterized.

In an embodiment, the systems of the present invention comprise the use of dynamic mathematical modeling to relate the expression levels of each of the genes in the cluster pool to each other. The model may be linear or nonlinear. In an embodiment, the modeling may comprise a Box-Jenkins Approach. For example, in certain embodiments, the modeling may comprises autoregressive exogenous (ARX) modeling or autoregressive (AR) modeling. Or, the modeling may comprise moving average modeling.

FIG. 7 shows an embodiment of the flow of information in a system comprising the software of the present invention. As used herein, a computer processor or CPU may include, for example, digital logic processors capable of processing input, executing algorithms, and generating output as necessary in response to the inputs received from the touch-sensitive input device. Such processors may include a microprocessor, such as an ASIC, and state machines. Such processors include, or may be in communication with, media, for example computer-readable media, which stores instructions that, when executed by the processor, cause the processor to perform the steps described herein.

Thus, in an embodiment, the starting point may comprise the image generated from a gene expression array or arrays (100). Alternatively, as for example where a radiolabeled probe is used, the input data may comprise a matrix corresponding to the amount of probe detected at each address. The data may be processed using an imaging system such as a imaging system commercially available from General Electric Corporation (110), or by other techniques, such as X-ray imaging or the like. The imaging system used may be custom-designed, or may be one of a number of commercially available packages.

Once the data has been collected (i.e., using the imaging system or other type of data collection system), it may be compiled (120) and/or transformed if necessary using any standard spreadsheet software such as Microsoft Excel, FOX-PRO®, Lotus, or the like. In an embodiment, the data are entered into the system for each experiment. Alternatively, data from previous runs are stored in the computer memory (160) and used as required.

At each point in the analysis, the user may input instructions via a keyboard (190), floppy disk, remote access (e.g., via the internet) (200), or other access means. The user may enter instructions including options for the run, how reports should be printed out, and the like. Also, at each step in the analysis, the data may be stored in the computer using a storage device common in the art such as disks, drives or memory (160). As is understood in the art, the processor (170) and I/O controller (180) are required for multiple aspects of computer function. Also, in a embodiment, there may be more than one processor.

The data may also be processed to remove noise (130) as described herein. In some cases, the user, via the keyboard (190), floppy disk, or remote access (200), may want to input variables or constraints for the analysis, as for example, the threshold for determining noise.

In the next step, a nonlinear independent component analysis (NICA) or nonlinear factor analysis (NLFA) (140) is performed as described above. In some cases, the user may want to input variables or constraints for the analysis, as for example, where the number of gene groups is known. Also, the user may choose the nonlinear independent component analysis software to be employed for the analysis. Examples of commercially available processing software suitable for microarray analysis include, but are not limited to MAT-LAB® (The MathWorks, Natick, Mass.), and SAS (SAS Institute, Inc., Cary, N.C.). For example, in one embodiment of the present invention, a prototype was coded using MAT-LAB® (without using the MATLAB® bioinformatics toolbox or any other MATLAB® function specialized for microarray processing). In an embodiment, the algorithm used for grouping the genes into clusters is designed to reduce or minimize computational memory required for matrix analysis. For example, for NICA, programs such as an unofficial nonlinear factor analysis Matlab package created by Laboratory of Computer and Information Science, Adaptive Informatics Research Center at Department of Computer Science and Engineering at the Helsinki University of Technology (available on line at the Helsinki University of Technology website) may be used.

Finally, the clusters defined by the nonlinear component analysis can be correlated to a biological response function and correlation analysis (150) (e.g., AR analysis) for genes within the cluster may be performed. Again, the user may want to input variables or constraints for the analysis, as for example, a limit for determining the significance of links between genes.

EXAMPLES

Example 1

Measurement of Gene Expression by Array Analysis for Genes Related to Bone Healing—Use of Linear ICA for Grouping Genes into Independent Components This experiment shows that ICA may be used as a method to group genes into independent components, without the need for any predetermined indication of the actual number of independent components required to explain the data. These experiments thus provide a basis for the development of non-linear ICA (NICA) and NLFA techniques.

FastICA (available from Helsinki University of Technology) implemented in MATLAB® 6.0 (The Mathworks, Inc., Natick, Mass.) was used for the analysis of gene expression data relating to bone healing. Although not as accurate as the traditional ICA methods, FastICA provides a much faster technique when large datasets are used. The hardware was a 1 GHz AMD ATHLON PROCESSOR® with 768 Mb memory. The input data was a series of four microarray measurements for the expression levels of genes of young rats during the bone fracture healing process. The data also included a starting non-fracture measurement.

The largest data set included 8,799 data points. For the removal of noise, the data from the control (the non-fracture reading) was subtracted from each subsequent data point (after fracture and during the healing process). Using a simple (i.e., non-optimized) filtering technique, series with changes less than 100 linear units of expression level were discarded. In the matrix array analyzer used (AFFYMETRIX®), expression levels below 100 are believed to be caused by machine noise and other sources of noise. Subtraction of noise left 4,315 series to consider. Due to the use of auto-correlation techniques for filtering (as discussed above) the filtering process is optimal and eliminates the noise-like patterns that have no significant biological basis.

ICA reduced the 4,315 components down to 530 independent components. As described above, the results of the modified FastICA algorithm (which is made hierarchical and dynamic) yields three matrices. The hierarchical nature of the revised version assets that the algorithm can start with n−1 independent components and add a new component based on the given signals. The first matrix defined by ICA contains a set of basis functions (i.e., s(t) in formulas above). The second matrix contains the mixing matrix (i.e., A in the formulas above), and the third matrix contains the separating matrix (W). Obtaining the actual independent components (signals) was done using the equations given above.

Figure 8:
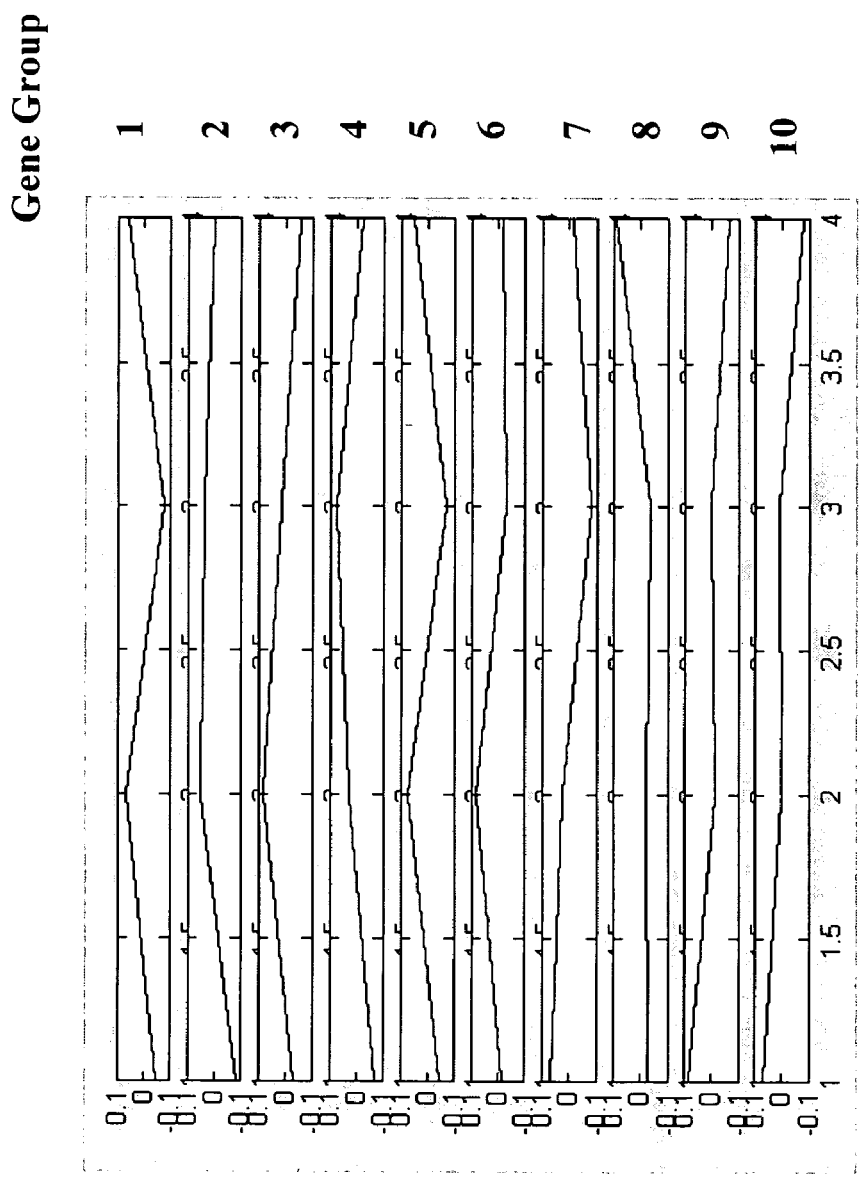
FIG. 8 shows ten separate independent gene clusters grouped using iterative linear ICA. The gene clusters were identified from an array experiment measuring relative gene expression for rats during the bone fracture healing process.

For this experiment, the sample size in time was K=4 (four time readings per gene) and the mean of the measured signals, x(t), was subtracted out. Subtracting out the means makes the figures easier to read and eliminates the chances of overweighting a gene due to baselines. The ICA signal components, s(t), were then plotted. Some of the components for this experiment are shown in FIG. 8, where the vertical axis is the amplitude of the normalized expression level and the horizontal axis is time. It can be seen that for this dataset, each of the independent components shows a different expression profile.

The next task was to determine what genes make up a given pathway. For this data, the maximum mixing coefficient was over 2,000 and the minimum mixing coefficient was under −2,100. The number of genes identified as being part of the identified group depends in part on the cutoff value used. If values of 20% of the maximum or minimum were chosen, the number of contributing genes was 750. Choosing a cutoff value of 5% reduced the count to 94. The 94 genes that make up pathway number 1, are listed in Table 1, below.

Figure 9:
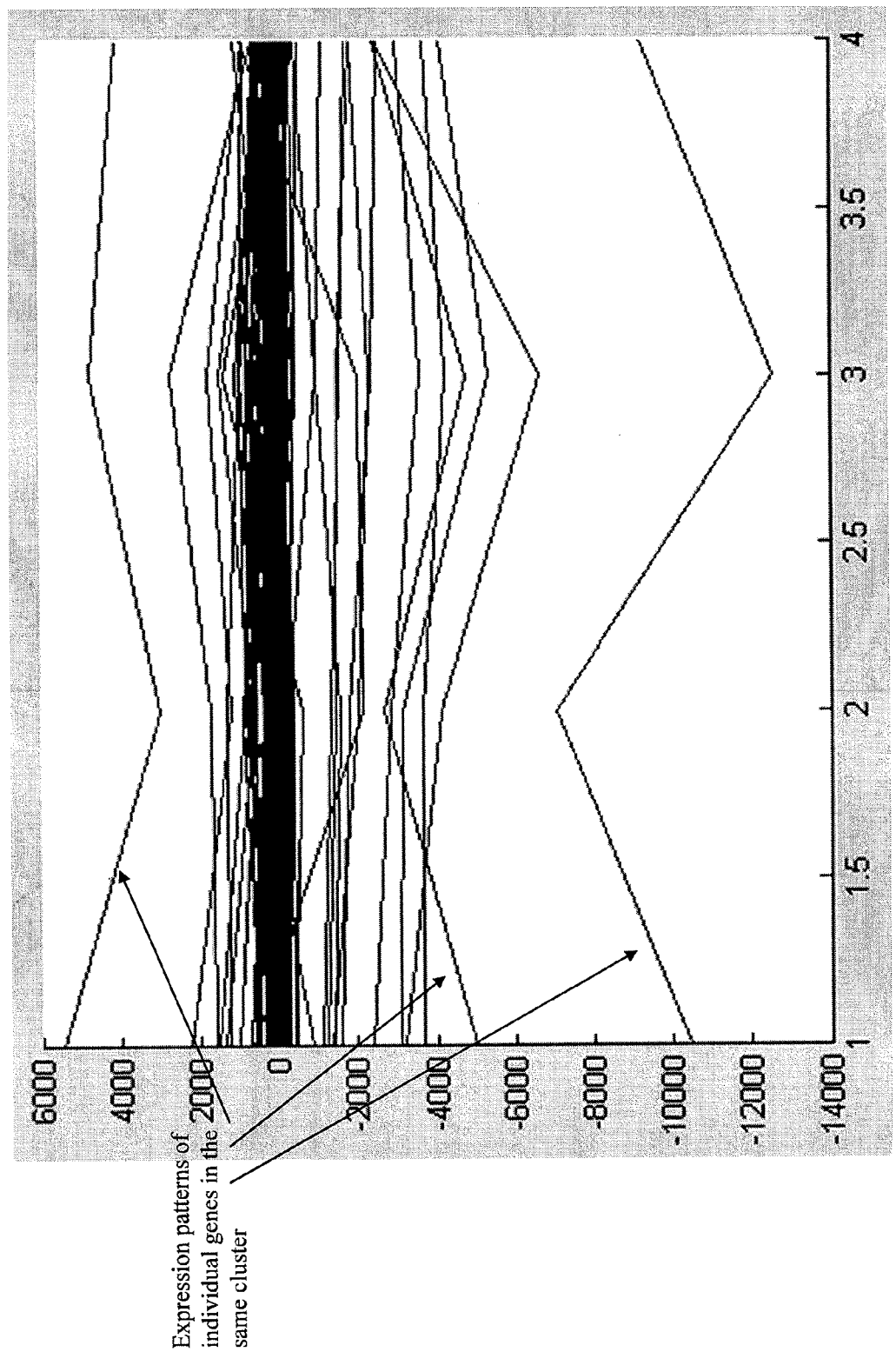
FIG. 9 shows relative expression as a function of time as derived for the 94 expressed genes in the first independent component (i.e., gene cluster) of FIG. 3 (Gene group 1) in accordance with an embodiment of the present invention.

FIG. 9 shows a composite of all 94 signals for these genes. Although the figure is too compressed in some regions to show correlations for many of the genes, some of the outer sequences can be seen to have highly correlated (or anti-correlated) expression profiles. The gene names used in Table 1 are the standard names used in public databases such as the data base available as the rat genome database at the Medical College of Wisconsin website.

TABLE 1

Genes Identified as Group 1 by ICA

| Gene ID | Gene Name |
| --- | --- |
| 125 | rc_AA819708_s_at |
| 192 | M24604_g_at |
| 238 | rc_AA875107_at |
| 282 | rc_AA899854_at |
| 287 | rc_AA944397_at |
| 309 | rc_AI229620_s_at |
| 384 | AF048687_s_at |
| 424 | D14014_at |
| 600 | L03294_at |
| 611 | L24896_s_at |
| 622 | J02585_at |
| 683 | U53922_at |
| 714 | X06827_g_at |
| 734 | U53855_at |
| 769 | D00680_at |
| 788 | M14050_s_at |
| 947 | X53363cds_s_at |
| 956 | X62086mRNA_s_at |
| 992 | Y13336cds_g_at |
| 1196 | AB018049_s_at |
| 1630 | AJ001929_s_at |
| 1668 | AJ009698_at |
| 1879 | D30804_at |
| 1906 | D42116_s_at |
| 1907 | D42137exon_s_at |
| 1916 | D45247_g_at |
| 1964 | D85183_s_at |
| 1966 | D85435_g_at |
| 2075 | L10652_at |
| 2110 | L14462_at |
| 2144 | L27843_s_at |
| 2151 | L31394exon_s_at |
| 2231 | M22340cds#1_s_at |
| 2459 | S61868_g_at |
| 2472 | S63233_g_at |
| 2512 | S69315_at |
| 2518 | S69874_s_at |
| 2525 | S71021_s_at |
| 2590 | S78217_s_at |
| 2591 | S78218_at |
| 2667 | U02506UTR#1_s_at |
| 2998 | X14323cds_at |
| 3098 | X59736mRNA_at |
| 3123 | X62145cds_g_at |
| 3144 | X62951mRNA_s_at |
| 3223 | X90475cds_at |
| 3431 | M74494_g_at |
| 3654 | LI9180_at |
| 3815 | X72914_at |
| 4133 | AB012234_at |
| 4171 | S54008_i_at |
| 4245 | M15882_g_at |
| 4523 | rc_AI639060_at |
| 5058 | rc_AA800745_at |
| 5138 | rc_AA945611_at |
| 5273 | rc_AI010480_at |
| 5362 | rc_AI059963_at |
| 5470 | rc_AI102031_g_at |
| 5495 | rc_AI103957_at |
| 5562 | rc_AI172162_at |
| 5563 | rc_AI172247_at |
| 5596 | rc_AI176589_g_at |
| 5637 | rc_AI179610_at |
| 5717 | rc_AI232477_s_at |
| 5797 | M25073_at |
| 5820 | K02815_s_at |
| 5967 | J04993_at |
| 6177 | U24150_at |
| 6456 | X52840_r_at |
| 6534 | D43623_g_at |
| 6582 | D10874_g_at |
| 6603 | X94551_at |
| 6719 | D78308_g_at |
| 6721 | D78359_at |
| 6749 | J04793_at |
| 6868 | AF016296_at |
| 7060 | rc_AA859536_at |
| 7071 | rc_AA859581_at |
| 7290 | rc_AA874848_s_at |
| 7499 | rc_AA875665_g_at |
| 7607 | rc_AA685178_at |
| 7618 | rc_AA891054_at |
| 7630 | rc_AA891171_s_at |
| 7655 | rc_AA891302_g_at |

TABLE 1-continued

Genes Identified as Group 1 by ICA

| Gene ID | Gene Name |
|---------|-----------|
| 7753 | rc_AA891797_at |
| 7755 | rc_AA891800_g_at |
| 7927 | rc_AA892388_at |
| 8266 | rc_AA893846_at |
| 8340 | rc_AA894207_g_at |
| 8396 | rc_AA799423_at |
| 8585 | rc_AA799861_g_at |
| 8622 | rc_AA800029_at |
| 8668 | rc_AA800250_at |
| 8698 | rc_AA800566_g_at |

Example 2

Identification of Genes within Independent Component Groups for S. Cerevisiae Using AR Modeling In this example, microarray gene expression data of the budding yeast S. Cerevisiae was analyzed by AR modeling to identify the mRNA transcript levels during the cell cycle of the budding yeast S. Cerevisiae. To obtain synchronous yeast culture, cdc28-13 yeast cells were arrested in late G1 by raising the temperature to 37° C., and then reinitiating the cell cycle by shifting cells to 25° C. Cells were collected at 17 time points taken at 10 min intervals, covering nearly two cell cycles (Cho et al, Molecular Cell, 2:65-73, 1998). Genes which have been activated in each phase of cell cycle (Early G1 phase, Late G1 phase, S phase, G2 phase or M phase) have been previously identified (Cho et al., Molecular Cell, 2:65-73, 1998) based on the functionality of the genes in each phase. Thus, it is known that the genes involved in the cell cycle process can be divided into five clusters depending upon the stage in which they are active.

AR modeling was applied to the data to discover the effect that each gene has on itself and other genes in the next phase of the cell cycle. As described above, in this analysis, gene expression is considered to be the output of the AR model and there are no inputs (since there is no perturbation). Since the number of genes was large, each cluster was assumed to be one independent component, and the AR model was trained to relate the independent components of clusters to each other.

The model parameters (i.e., coefficients) were estimated using the independent components as the training set. In order to see how well the resulting model could dynamically relate the expression level of each individual gene to the other genes, the model was used to predict the expression level of individual genes from each cluster. The predicted and true values of the expression levels for these genes are compared in FIG. 4, panels A-J. As can be seen, the model predicted the expression level accurately. The full gene names for the genes described in FIG. 4 can be found in Cho et al., 1998.

Example 3

Modeling and Prediction of Cell Cycle Dynamic Pathway Using NICA and AR Modeling The dataset used were again taken from the budding yeast S. Cerevisiae cell cycle dataset of Cho et al., 1998. The number of total genes considered in this experiment was 40. In order to train the model, the first ten time points of each component were used as training data to find the NICA and AR models. Then, the expression values of each component and as a result all individual genes, were predicted for all time steps. Since the number of time points in the training data was small (i.e., eight steps in each cycle), in order to minimize the number of parameters, the degree of the model was set to one.

As described herein, training of an AR model is equivalent to the estimation of $a_{ij}$ coefficients, where i=1, . . . , 5, and j= 1, . . . , 5. Since the degree of the model is set to 1 for all genes, the third index of the parameters is dropped. After training with the first ten time points the following values for $a_{ij}$ coefficients re obtained as:

$$A = \begin{bmatrix} -1.045 & -0.970 & 0.634 & -36.803 & -19.920 \\ 0.848 & 0.033 & -0.606 & 28.340 & 40.800 \\ 0.0860 & 0.919 & -0.780 & 26.539 & 20.936 \\ -0.0022 & 0.0004 & 0.0135 & -0.480 & -0.285 \\ 0.0065 & 0.0124 & -0.0233 & 0.433 & 0.474 \end{bmatrix}$$

Using each row of this matrix one can predict the value of one component in the next time step based on the values of the all components in the previous times. For example, for the first component, the model can be written as:

$$y_1(t) = -1.045 y_1(t-1) - 0.970 y_2(t-1) + 0.634 y_3(t-1) - 36.803 y_4(t-1) - 19.920 y_5(t-1) \quad (32)$$

Similar equations can be obtained form the matrix given above for other components. As mentioned above, the first 10 points of the data was used to train the model, and the capabilities of the model in predicting the correct values of expression in future samples are tested against all the time steps, which includes 17 time samples. To test and validate the performance of the model in estimating the future values of individual gene, the nonlinear factor analysis method was applied to all genes and after producing the major components of genes, the network of NLFA is used to predict the expression value of each single gene in the future time steps.

The prediction results for some of the genes are shown in FIG. 5. As can be seen in FIG. 5, the predicted values matched very well with the true expression values of genes indicating that the model can successfully predict the trend of the genes expressions based on the expression values of all genes at the previous times.

In addition, the method allows depiction of a network between five components (i.e., genes in each of the five cell cycles) to represent the dynamic pathway of cell cycle process. Such a network shows the effect of each prototype on itself and on other genes in the next time step. Since showing all 25 links and arrows would complicate the graph, in FIG. 6, only the effect of all components on the first component are shown. It is important to note that in the resulting dynamic graph, there is a one-step delay in the effect of all components on component one (i.e. the components determine the expression value of the component one in the next time point).

Example 4

Comparison of Linear and Nonlinear Modeling and Prediction of Cell Cycle Dynamic Pathways a. Theoretical Gene Networks To evaluate the proposed methods and evaluate the advantages/disadvantages of the nonlinear model over linear models (e.g., $x(t) = A_{rec} x(t-1) + B_{rec}$; Davish et al., 2005), a synthetic gene network was produced using nonlinear mathematical equations. Then the proposed methods to predict the value of synthetic gene expression data in future times. Two types of nonlinearity were considered to generate the gene networks. In the first set of synthetic time series data was produced using a nonlinearity of type polynomial. For the second synthetic time series, nonlinearities typically used to model the nonlinear effects of translation and transcription were used. The second model is implanted as a set of differential equations.

The numbers of genes in both these simulations were 60, 65 and 115 for in different experiments. Regarding the length of the time series, the number of time steps was limited to 30. In both simulations, the number of regulators for each gene also varies from 5 to 10. For the polynomial synthetic data, the equation used to generate the synthetic time series was:

$$x_i(t) = A x_{reg}(t-1)^2 + B x_{reg}(t-1) \tag{32}$$

where x(t) is the expression value of gene i at time t and $x_{reg}(t)$ is the expressions of the regulators of gene i (which is a subset of all genes) at time t. The simulations to generate the network have been implemented in MATLAB. It was verified that the obtained network was stable and reaches a steady state condition after some time steps. Thus, the sampling rate was chosen in a way to have 30 time steps from time 0 to the time of steady state condition.

In the second group of simulations, a set of differential equations typically used to simulate the gene expressions (Sakamoto et. al 2001), have been used. The set of time-series data is the sampled version of the following multidimensional differential equations:

$$dx_i(t)/dt = a_i x_1(t) x_2(t) x_3(t) \ldots x_k(t) \tag{33}$$

where $x_i$ represents the expression value of gene i and $x_1$, $x_2, \ldots x_k$ are the regulators of the ith gene. As mentioned above, this differential equation has been chosen because the literature identifies such differential equations as reasonable models of nonlinear dynamics in gene regulatory networks (Sakamoto et. al 2001). It was expected that these formulations can provide a sufficiently realistic nonlinear model of the gene expression time-series. The number of differential equations in the second model equals to the number of genes. This set of differential equations has been solved using numerical methods implemented by ODE commands in MATLAB. The number of potential regulators for each gene has been fixed to be set to a number less than or equal to 5, i.e. k=5. Since the data have been generated by differential equations that are continuous in nature, sampling should be done to obtain discrete-time data. The sampling rate was chosen so that the Nyquist rate is observed. The number of time steps in discrete data is set to be 30.

To evaluate the proposed method for each of the synthetic datasets, the resulting time-series for each gene were divided into training and testing sets. The training set includes time series data for all genes but only for two third of time steps (i.e. 20) and the testing set includes the time series in entire of the signal.

Figure 10A:
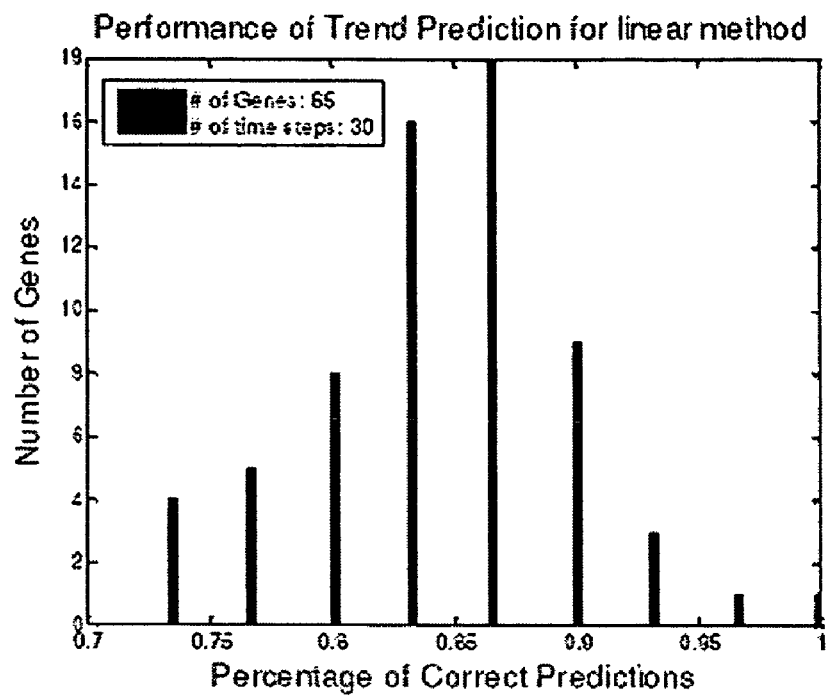
FIG. 10 shows a histogram of correct model predictions for linear and nonlinear models on synthetic data generated using polynomial equations where panel 10A shows a linear method for 65 genes; panel 10B shows a nonlinear method for 65 genes; panel 10C shows a linear method for 115 genes; and panel 10D shows a nonlinear method for 115 genes in accordance with an embodiment of the present invention.
Figure 10:
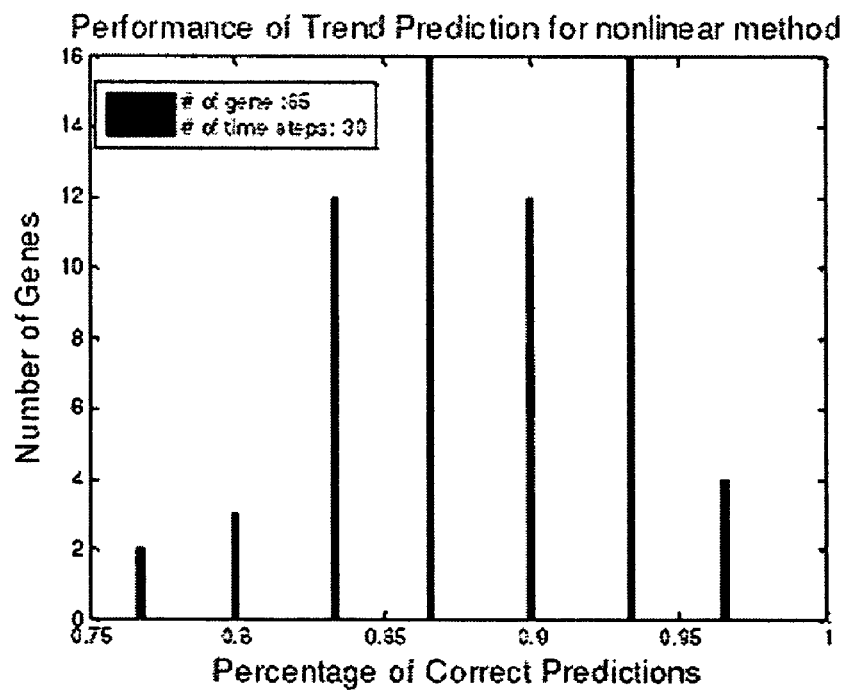

To evaluate the linear and nonlinear methods, the number of time steps at which the models can correctly predict the expression value of each gene at the next time step was computed. FIG. 10 shows the histogram of percentages of correct predictions for both nonlinear and linear methods using the polynomial model. FIG. 11 shows the histogram of percentages of correct predictions for both nonlinear and linear methods using the model generated with the differential equation. A correct prediction means that the algorithm can correctly predict that in the next time step the gene expression value would increase or decrease in value. Specifically, considering the high noise nature of gene expression measurement, the main purpose of this procedure is to predict the overall pattern of mRNA level of each gene in following times as opposed to the exact expression values. The histograms show the percentage of the time steps (out of 30 steps) in which the method can correctly predict the pattern of variation in expression value of each gene (increase or decrease) from time t to time t+1. These percentages are provided for simulations with a number of time series having different number of genes (65 and 115). For instance when the value of 93% is 16 in a histogram in FIG. 2, this means that for 16 genes in 93% of time steps (i.e. 28 out of 30 time steps) the model correctly predicts the pattern of mRNA level from each time t to time t+1.

Figure 10C:
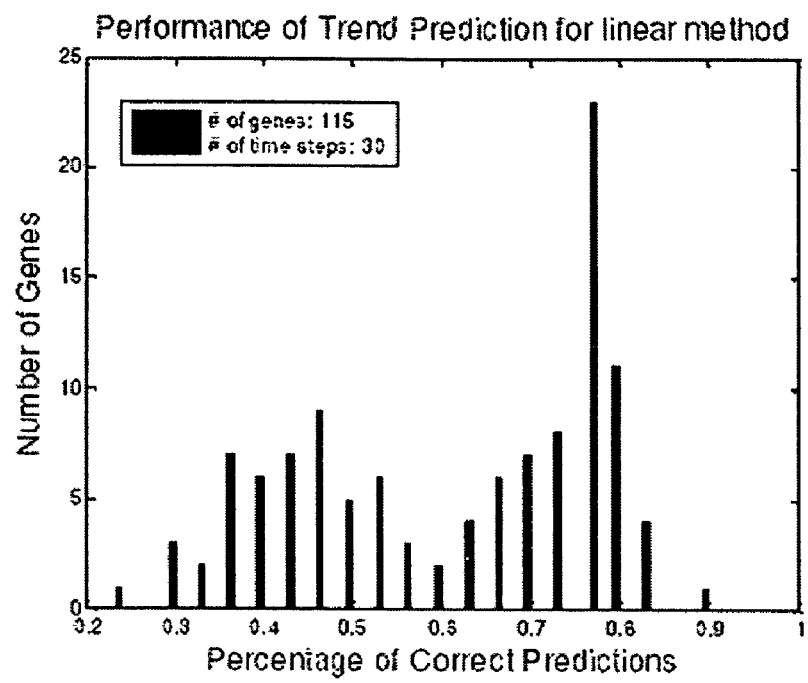
Figure 10D:
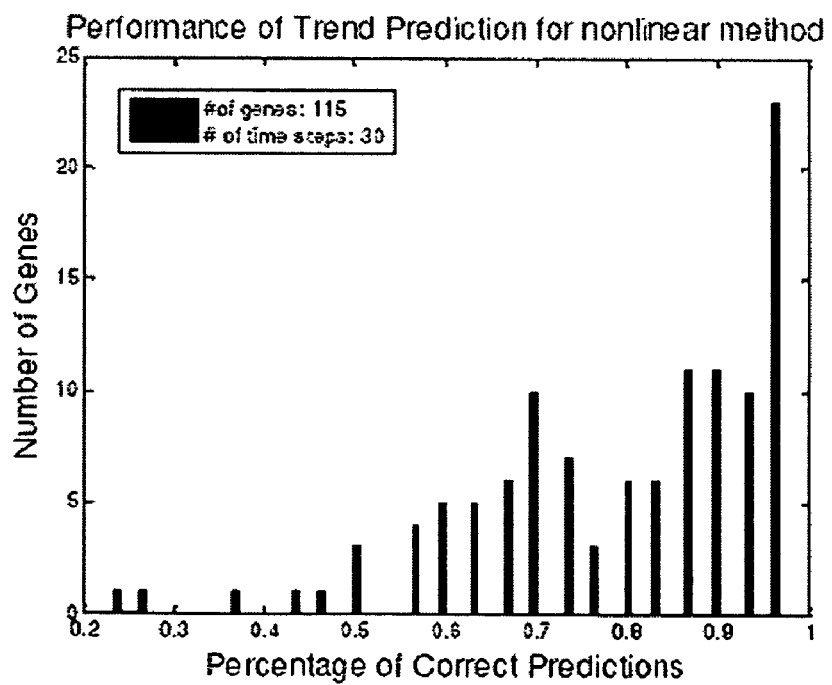
Figure 11A:
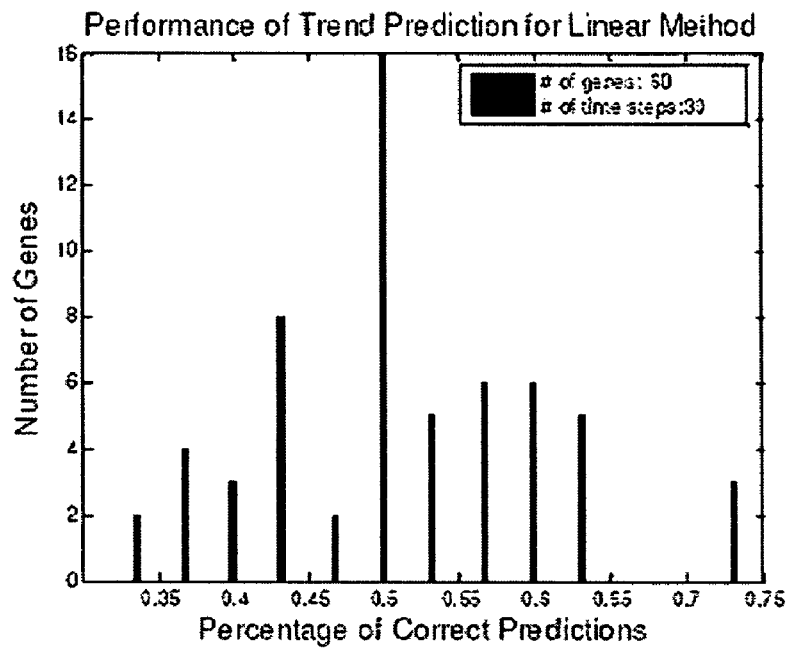
FIG. 11 shows a histogram of correct model predictions for linear and nonlinear models on synthetic data generated using a nonlinear differential equation where panel 11A shows a linear method for 60 genes, and panel 11B shows a nonlinear method for 65 genes in accordance with an embodiment of the present invention.
Figure 11B:
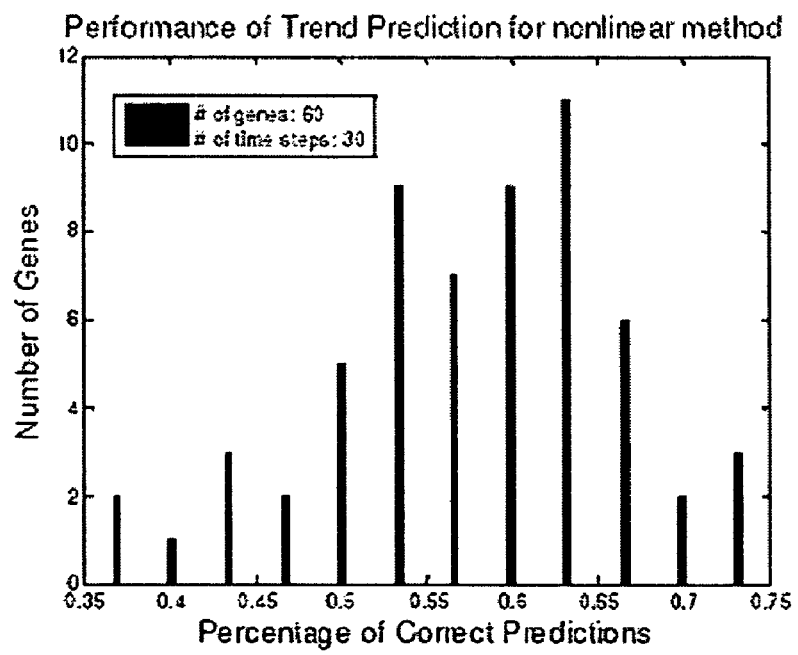

As it can be seen from the graphs, the nonlinear method has higher peaks in highest percentages, i.e. the nonlinear model can more accurately predict the future patterns for higher percentage of time steps for more genes. This superiority of nonlinear method holds for both cases of 65 (FIGS. 10A and 10B) and 115 genes (FIGS. 10C and 10D). For example, in the case of 65 genes (FIGS. 10a and 10b), it can be seen that for 23 genes, the nonlinear model can correctly predict the gene expression patterns in over 95% of the time steps. The linear model was unable to predict the expression patterns for any gene in more than 90% of the time steps. FIG. 11 shows the similar result for the case of synthetic gene network generated using the above mentioned nonlinear differential equations. Here again it can be seen that the nonlinear method (FIG. 11B) hits a higher percentage of correct predictions for most of the genes in compare with linear method (FIG. 11A).

b. Cell Cycle Data

Figure 12A:
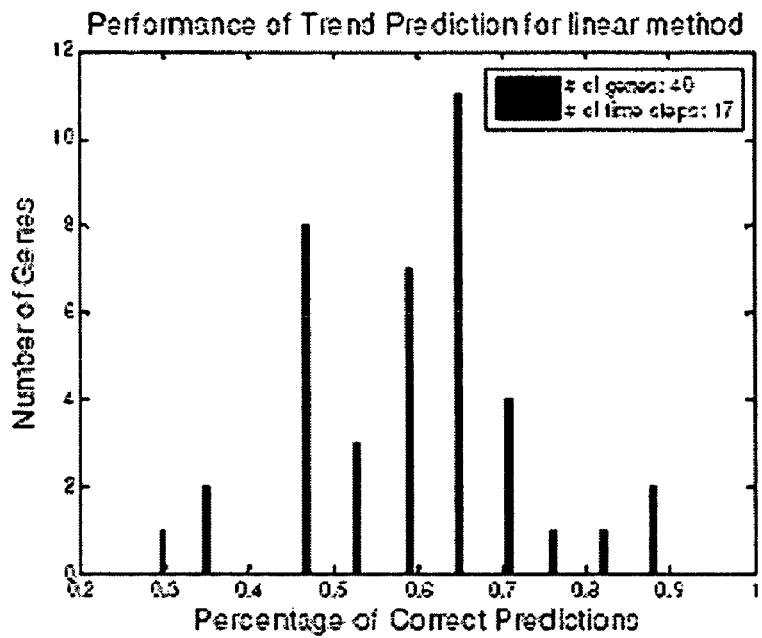
FIG. 12 shows a histogram of correct model predictions for linear and nonlinear models on yeast S. cerevisiae cell cycle data panel 12A shows a linear method, and panel 12B shows a nonlinear method in accordance with an embodiment of the present invention.
Figure 12B:
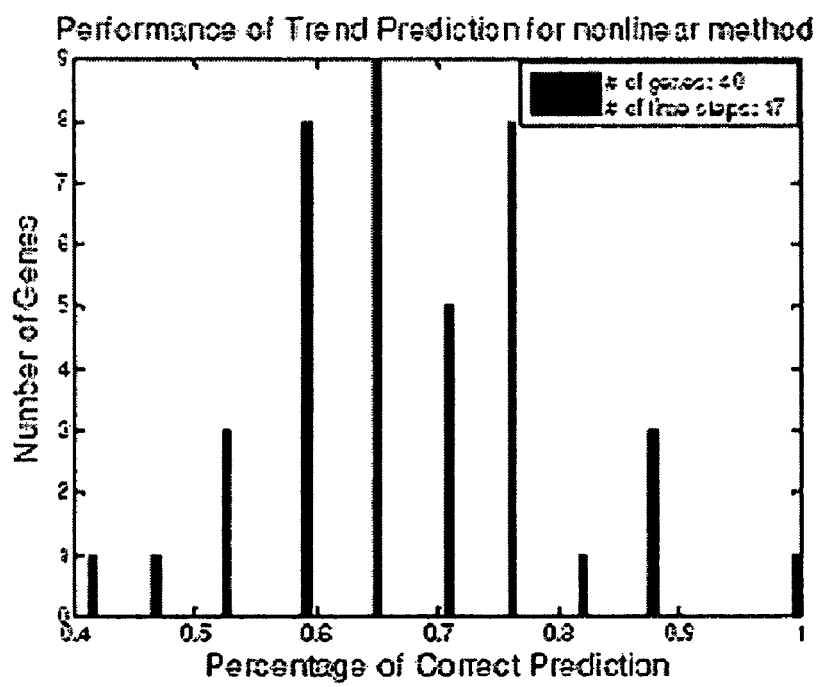

For the yeast S. Cerevisiae cell cycle data, the expression value of the individual genes in future times was predicted using both linear and nonlinear methods. FIG. 12 depicts the histogram of correct prediction for linear and nonlinear methods. As it can be seen from FIG. 12, the histogram corresponding to nonlinear method (FIG. 12B) had higher value for peaks in higher percentages compared with the histogram of the linear method (FIG. 12A), indicating that a nonlinear methods provide reliable and accurate estimation of gene networks.

Example 5

Stability Analysis of the System

To analyze the stability of the model, we consider the AutoRegressive model which has been applied on the factors of nonlinear independent factor analysis. Due to the fact that the degree of the model for each gene cluster was assumed to be 1, the AR model we developed for the cell cycle system describes the following discrete state space model:

$$Y(t) = AY(t-1) + e(t) \tag{34}$$

where Y(t) is the vector of factors (trends) at time t. In the above model, the values of the factors play the role of the states in the state model. As in any other dynamic system, it was of interest to perform an assessment of the system stability.

Figure 13:
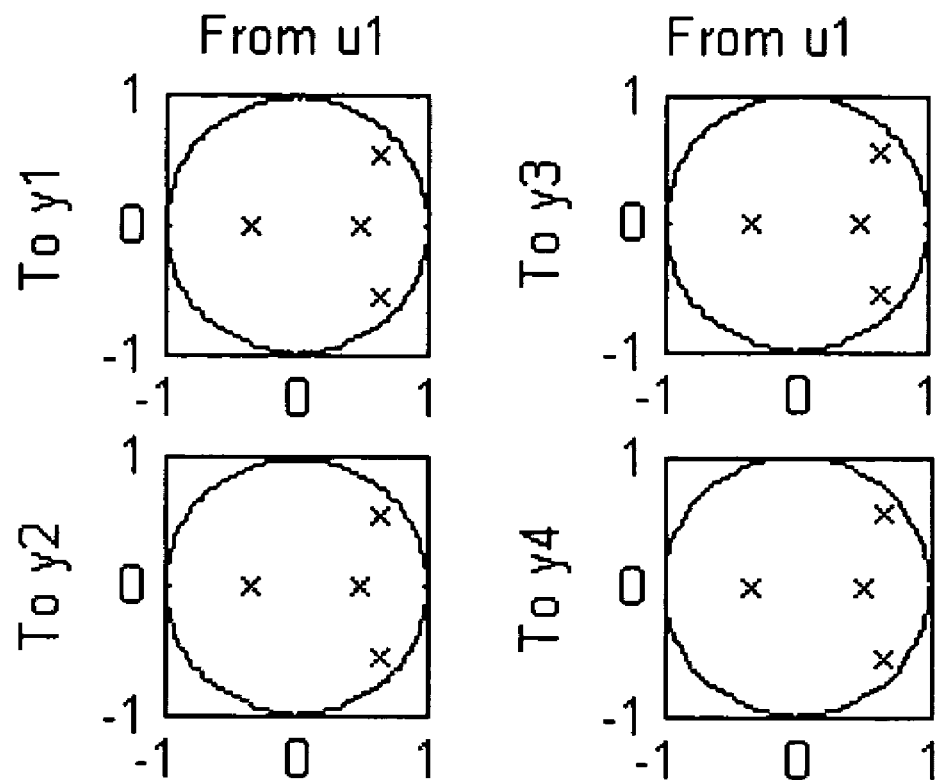
FIG. 13 shows a pole diagram of the ARX model in accordance with an embodiment of the present invention.

A straightforward approach in evaluating the stability in Lyapunov sense is examining the eigenvalues of matrix A, which are indeed the poles of the system. Every equilibrium state of the model described in the equation above is stable if and only if the magnitude of all eigenvalues of A are less than or equal to 1. If there is one or more eigenvalues whose magnitude equals 1, then the system oscillates. Even though oscillation might be undesirable in many man-made systems, the survival of many biological systems (such as cell cycle)

highly depends on it. FIG. 13 shows the poles of the system. As it can be seen in FIG. 13, two poles of the system lie well inside unit circle and the other two are almost on the unit circle. Having two poles on the unit circle describes why the cell cycle system is an oscillating and repetitive process. Since the auto regressive equation was obtained using only 10 time points, there might be a small error in estimating the location of the poles.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A computer-implemented method for analyzing gene expression wherein the method comprises the steps of:
   using a specifically programmed computer to receive compiled data comprising a plurality of measured gene expression signals; and
   using the specifically programmed computer to analyze the compiled data using the substeps of:
   (i) using the specifically programmed computer to apply a nonlinear independent component analysis to the compiled data to identify a plurality of independent components into which the data may be grouped;
   (ii) using the specifically programmed computer to apply autoregressive or autoregressive exogenous modeling to the identified independent components to describe an expression profile model for each independent component identified in step (i); and
   (iii) using the specifically programmed computer to apply the nonlinear independent component analysis in an inverse manner to the expression profile model for an individual component as derived in step (ii) to predict the expression values of an individual gene.

2. The computer-implemented method of claim 1, wherein the autoregressive or autoregressive exogenous modeling in step (ii) is used to predict the levels of expression of individual genes over time.

3. The computer-implemented method of claim 1, wherein the autoregressive or autoregressive exogenous modeling in step (ii) applies data derived from a subset of the time points for which data is available and uses that subset of data to predict gene expression over a larger period of time.

4. The computer-implemented method of claim 3, wherein the autoregressive or autoregressive exogenous modeling in step (ii) is derived using data derived from a subset of data derived from the earliest time points for which data is available.

5. The computer-implemented method of claim 1, wherein the nonlinear independent component analysis performs a nonlinear factor analysis.

6. The computer-implemented method of claim 1, wherein the number of independent components is correlated to a pattern of gene expression for at least one cell type.

7. The computer implemented method of claim 1, wherein the method correlates at least one of the measured signals, x, to the underlying sources, s, generating the signal, and experimental noise, n, as a function of time, t, such that $x(t)=f(s(t))+n(t)$, where $f(.)$ describes the nonlinear mapping.

8. The computer implemented method of claim 1, wherein the method of nonlinear independent component analysis comprises using a neural network defined as: $x(t)=g(s(t))+n(t)=B \tan h(As(t)+a)+b+n(t)$, wherein the neural network is used in combination with back propagation to model the nonlinearity of the system such that A, B, a, and b are determined for the data set.

9. The computer-implemented method of claim 1, wherein the plurality of measured signals comprise data generated by hybridization of a plurality of known DNA sequences to mRNA isolated from at least one cell type.

10. The computer-implemented method of claim 9, wherein the plurality of known DNA sequences are arranged to form a solid-state array.

11. The computer-implemented method of claim 1, wherein a number of independent components into which the compiled data may be grouped, n, is estimated as a preset number, $n_0$.

12. The computer-implemented method of claim 11, wherein the compiled data are evaluated by sequentially increasing the number of independent clusters from a minimum number, $n_0$, and determining the relative fit of the data using $n_0$ as compared to the new value of n.

13. The computer-implemented method of claim 12, wherein the number of clusters are increased incrementally by one for each evaluation, such that the number of independent clusters into which the compiled data may be grouped increases by one at each step from $n_0$, to $n_0+1$, to $n_0+2$, until the optimum number of groups ($n_{opt}$) is determined.

14. The computer-implemented method of claim 1, further comprising using a specifically programmed computer to perform hierarchical nonlinear component analysis such that the complexity of the computational analysis is reduced as the analysis proceeds by removing as inputs data that has been described at earlier stages of the analysis from the set of data points still remaining to be characterized.

15. The computer-implemented method of claim 1, further comprising using a specifically programmed computer to normalize the variance of the compiled data.

16. The computer-implemented method of claim 1, wherein step (ii) further comprises using a specifically programmed computer to determine if there is a cross-correlation between at least two measured signals within a component group, wherein a positive cross-correlation comprises the situation in which the expression of one gene in the group is statistically correlated with the expression of a second gene in the same group.

17. The computer-implemented method of claim 16, wherein the correlation between genes within a group is expressed as a mathematical model describing relative levels of gene expression.

18. The computer-implemented method of claim 1, wherein the autoregressive exogenous model comprises the expression $y_i=f(y_1, y_2, \ldots y_P, u_1, u_2 \ldots u_M)+e$, where $y_1, y_2 \ldots y_P$, is the expression of genes $1, 2, \ldots P$; $u_1, u_2 \ldots u_M$, corresponds to environmental factors $1, 2 \ldots M$, and experimental noise is defined by e.

19. The computer-implemented method of claim 17, further comprising the step of using a specifically programmed computer to remove statistically weak links from the model.

20. A system for analyzing gene expression for at least one cell type comprising:
   a computer-readable medium; and
   a specifically programmed computer in communication with the computer-readable medium, the specifically programmed computer configured to:
   receive compiled data comprising a plurality of measured gene expression signals from the at least one cell type;
   analyze the compiled data by:

(i) applying a nonlinear independent component analysis to the compiled data to identify a plurality of independent components into which the data may be grouped;
(ii) applying autoregressive or autoregressive exogenous modeling to the identified independent components to describe an expression profile model for each independent component identified in step (i); and
(iii) applying the nonlinear independent component analysis in an inverse manner to the expression profile model for an individual component as derived in step (ii) to predict the expression values of an individual gene; and transmit the results of the analysis.

21. A non-transitory computer-readable medium on which is encoded programming code for analyzing gene expression from a plurality of data comprising measured gene expression signals, wherein the programming code comprises:

programming code for receiving data that comprises a plurality of measured gene expression signals from at least one cell type;
programming code for applying a nonlinear independent component analysis to the data to identify a plurality of independent components into which the data may be grouped;
programming code for applying autoregressive or autoregressive exogenous modeling to the identified independent components to describe an expression profile model for each identified independent component; and
programming code for applying the nonlinear independent component analysis in an inverse manner to the expression profile model for an individual component to predict the expression values of an individual gene; and
programming code for transforming the results of the analysis into a report for a user.

* * * * *